(12) United States Patent
Dreyfus et al.

(10) Patent No.: US 10,527,601 B2
(45) Date of Patent: Jan. 7, 2020

(54) METHOD FOR DETERMINING THE LOCATION, SIZE, AND FLUID COMPOSITION OF A SUBSURFACE HYDROCARBON ACCUMULATION

(71) Applicants: Sebastien L. Dreyfus, Houston, TX (US); Michael Lawson, Houston, TX (US); Aaron B. Regberg, Houston, TX (US); A. Lucie N'Guessan, Houston, TX (US); Robert J. Pottorf, Houston, TX (US); Steven R. May, Missouri City, TX (US); Amelia C. Robinson, Houston, TX (US); William G. Powell, Houston, TX (US); Sumathy Raman, Annandale, NJ (US)

(72) Inventors: Sebastien L. Dreyfus, Houston, TX (US); Michael Lawson, Houston, TX (US); Aaron B. Regberg, Houston, TX (US); A. Lucie N'Guessan, Houston, TX (US); Robert J. Pottorf, Houston, TX (US); Steven R. May, Missouri City, TX (US); Amelia C. Robinson, Houston, TX (US); William G. Powell, Houston, TX (US); Sumathy Raman, Annandale, NJ (US)

(73) Assignee: ExxonMobil Upstream Research Company, Spring, TX (US)

( * ) Notice: Subject to any disclaimer, the term of this patent is extended or adjusted under 35 U.S.C. 154(b) by 1075 days.

(21) Appl. No.: 14/350,887

(22) PCT Filed: Nov. 9, 2012

(86) PCT No.: PCT/US2012/064551
§ 371 (c)(1),
(2) Date: Apr. 10, 2014

(87) PCT Pub. No.: WO2013/071188
PCT Pub. Date: May 16, 2013

(65) Prior Publication Data
US 2014/0288853 A1    Sep. 25, 2014

Related U.S. Application Data

(63) Continuation-in-part of application No. PCT/US2012/052542, filed on Aug. 27, 2012.
(Continued)

(51) Int. Cl.
*G01N 33/24* (2006.01)
*G01V 9/00* (2006.01)
(Continued)

(52) U.S. Cl.
CPC .............. *G01N 33/241* (2013.01); *G01N 1/00* (2013.01); *G01N 29/14* (2013.01); *G01V 1/38* (2013.01);
(Continued)

(58) Field of Classification Search
CPC . G01V 9/007; G01V 1/38; G01V 3/08; G01V 3/081; G01V 9/005; G01V 8/02;
(Continued)

(56) References Cited

U.S. PATENT DOCUMENTS

| | | |
|---|---|---|
| 3,571,591 A | 3/1971 | Bradley et al. |
| 3,835,710 A | 9/1974 | Pogorski |

(Continued)

FOREIGN PATENT DOCUMENTS

| | | |
|---|---|---|
| EP | 2113796 | 11/2009 |
| GB | 2478511 | 9/2011 |

(Continued)

OTHER PUBLICATIONS

Hohl, "DCO Energy, Environment and Claimate workshop", 2010, pp. 1-37.*

(Continued)

*Primary Examiner* — Mohamed Charioui
*Assistant Examiner* — Eyob Hagos
(74) *Attorney, Agent, or Firm* — ExxonMobil Upstream Research Company—Law Department

(57) ABSTRACT

A method is disclosed for determining a presence, type, quality and/or volume of a subsurface hydrocarbon accumulation from a sample related thereto. The method may include obtaining sample data associated with a subsurface hydrocarbon accumulation, wherein the sample data
(Continued)

includes a noble gas signature, a clumped isotope signature and/or a ecology signature. From the signatures, relationships between the noble gas signature; the clumped isotope signature and the ecology signature are identified and stored in memory.

22 Claims, 5 Drawing Sheets

Related U.S. Application Data

(60) Provisional application No. 61/558,822, filed on Nov. 11, 2011, provisional application No. 61/595,394, filed on Feb. 6, 2012, provisional application No. 61/616,813, filed on Mar. 28, 2012.

(51) Int. Cl.
| | |
|---|---|
| *G01N 1/00* | (2006.01) |
| *G01N 29/14* | (2006.01) |
| *G01V 1/38* | (2006.01) |
| *G01V 3/08* | (2006.01) |
| *B63G 8/00* | (2006.01) |
| *G01V 11/00* | (2006.01) |
| *G01V 8/02* | (2006.01) |
| *G01V 5/00* | (2006.01) |
| *G01V 8/00* | (2006.01) |
| *G06F 19/00* | (2018.01) |

(52) U.S. Cl.
CPC ............... *G01V 3/08* (2013.01); *G01V 3/081* (2013.01); *G01V 9/005* (2013.01); *G01V 9/007* (2013.01); *B63G 8/001* (2013.01); *G01V 5/00* (2013.01); *G01V 8/00* (2013.01); *G01V 8/02* (2013.01); *G01V 11/00* (2013.01); *G06F 19/00* (2013.01)

(58) Field of Classification Search
CPC . G01V 11/00; G01V 8/00; G01V 5/00; G01N 1/00; G01N 29/14; G01N 33/241; G06F 19/00
See application file for complete search history.

(56) References Cited

U.S. PATENT DOCUMENTS

| | | |
|---|---|---|
| 3,862,576 A | 1/1975 | Pogorski |
| 3,961,187 A | 6/1976 | Barringer |
| 4,001,764 A | 1/1977 | Holland et al. |
| 4,378,055 A | 3/1983 | Bartz |
| 4,434,364 A | 2/1984 | Correa et al. |
| 4,560,664 A | 12/1985 | Demaison et al. |
| 4,833,915 A | 5/1989 | Radd et al. |
| 5,439,800 A | 8/1995 | Thompson |
| 5,798,982 A | 8/1998 | He et al. |
| 6,246,963 B1 | 6/2001 | Cross et al. |
| 6,509,566 B1 | 1/2003 | Wamsley et al. |
| 6,514,945 B1 | 2/2003 | Beyer et al. |
| 6,578,405 B2 | 6/2003 | Kleinberg et al. |
| 6,613,520 B2 | 9/2003 | Ashby |
| 6,645,769 B2 | 11/2003 | Tayebi et al. |
| 6,754,588 B2 | 6/2004 | Cross et al. |
| 6,810,332 B2 | 10/2004 | Harrison |
| 6,826,483 B1 | 11/2004 | Anderson et al. |
| 6,873,570 B2 | 3/2005 | Zhu et al. |
| 6,888,127 B2 | 5/2005 | Jones et al. |
| 6,985,841 B2 | 1/2006 | Barroux |
| 7,011,154 B2 | 3/2006 | Maher et al. |
| 7,124,030 B2 | 10/2006 | Ellis |
| 7,174,254 B2 | 2/2007 | Ellis |
| 7,210,342 B1 | 5/2007 | Sterner et al. |
| 7,249,009 B2 | 7/2007 | Ferworn et al. |
| 7,297,661 B2 | 11/2007 | Beyer et al. |
| 7,328,107 B2 | 2/2008 | Strack et al. |
| 7,337,660 B2 | 3/2008 | Ibrahim et al. |
| 7,387,021 B2 | 6/2008 | DiFoggio |
| 7,395,691 B2 | 7/2008 | Sterner et al. |
| 7,520,158 B2 | 4/2009 | DiFoggio |
| 7,526,418 B2 | 4/2009 | Pita et al. |
| 7,529,626 B1 | 5/2009 | Ellis |
| 7,596,480 B2 | 9/2009 | Fung et al. |
| 7,617,082 B2 | 11/2009 | Childs et al. |
| 7,687,769 B2 | 3/2010 | Indo et al. |
| 7,692,429 B2 | 4/2010 | MacGregor et al. |
| 7,704,746 B1 | 4/2010 | White et al. |
| 7,728,291 B2 | 6/2010 | Bello |
| 7,809,538 B2 | 10/2010 | Thomas |
| 7,969,152 B2 | 6/2011 | Velikhov et al. |
| 8,033,756 B2 | 10/2011 | Adamson |
| 8,071,295 B2 | 12/2011 | Ashby |
| 8,120,362 B2 | 2/2012 | Combee |
| 8,299,424 B2 | 10/2012 | Camilli |
| 8,316,934 B2 | 11/2012 | Pietrobon |
| 8,502,974 B2 | 8/2013 | Johnsen |
| 8,505,375 B2 | 8/2013 | Smalley |
| 8,577,613 B2 | 11/2013 | Bryant et al. |
| 8,695,703 B2 | 4/2014 | Dinariev et al. |
| 8,714,246 B2 | 5/2014 | Pop et al. |
| 2002/0120429 A1 | 8/2002 | Ortoleva |
| 2006/0154306 A1 | 7/2006 | Kotlar et al. |
| 2008/0040086 A1 | 2/2008 | Betancourt et al. |
| 2008/0059140 A1 | 3/2008 | Salmon et al. |
| 2008/0097735 A1 | 4/2008 | Ibrahim et al. |
| 2008/0099241 A1 | 5/2008 | Ibrahim et al. |
| 2008/0147326 A1 | 6/2008 | Ellis |
| 2009/0071239 A1 | 3/2009 | Rojas et al. |
| 2009/0150124 A1 | 6/2009 | Wilt et al. |
| 2010/0015612 A1 | 1/2010 | Pelham et al. |
| 2010/0086180 A1 | 4/2010 | Wallace |
| 2010/0153050 A1 | 6/2010 | Zumberge et al. |
| 2010/0155078 A1 | 6/2010 | Walters et al. |
| 2010/0257004 A1 | 10/2010 | Perlmutter et al. |
| 2010/0279290 A1* | 11/2010 | Sleat ............ C12Q 1/689 435/6.11 |
| 2011/0004367 A1 | 1/2011 | Saunders et al. |
| 2011/0030465 A1* | 2/2011 | Smalley ............ E21B 43/00 73/152.07 |
| 2011/0158041 A1* | 6/2011 | Moldoveanu ........ G01V 1/003 367/14 |
| 2011/0250582 A1* | 10/2011 | Gates ............ C09K 8/582 435/3 |
| 2011/0264430 A1 | 10/2011 | Tapscott et al. |
| 2011/0308790 A1 | 12/2011 | Strapoc et al. |
| 2012/0052564 A1 | 3/2012 | Shigeura et al. |
| 2012/0134749 A1 | 5/2012 | Darrah |
| 2013/0091925 A1* | 4/2013 | Darrah ............ G01V 5/06 73/23.35 |

FOREIGN PATENT DOCUMENTS

| | | |
|---|---|---|
| WO | 2003/012390 | 2/2003 |
| WO | 2004/025261 | 3/2004 |
| WO | 2007/008932 | 1/2007 |
| WO | 2008/100614 | 8/2008 |
| WO | 2010/151842 | 12/2010 |
| WO | 2011/136858 | 11/2011 |
| WO | 2011/159924 | 12/2011 |
| WO | 2012/052564 | 4/2012 |

OTHER PUBLICATIONS

Eiler, "Clumped isotope geochemistry the study of naturally occurring multiply substituted isotopologues", 2007, ScienceDirect, pp. 310-325.*

Auer, "High-level ab-initio calculation of gas-phase NMR chemical shifts and secondary isotope effects of methanol", 2008, pp. 330-332.*

(56) References Cited

OTHER PUBLICATIONS

Pinti, "Noble gases in crude oils from the Paris Basin, France: Implications for the origin of fluids and constraints on oil-water-gas interactions", 1995, pp. 3389-3402.*

Aeschbach-Hertig, W., et al., (2000), "Palaeotemperature reconstruction from noble gases in ground water taking into account equilibrium with entrapped air", *Nature*, 405, pp. 1040-1044.

Ballentine, C. J., et al., (2002), "Production, release and transport of noble gases in the continental crust", *Reviews in Mineralogy and Geochemistry*, 47, pp. 481-538.

Ballentine, C.J., et al., (2002), "Tracing Fluid Origin, Transport and Interaction in the Crust", *Reviews in Mineralogy and Geochemistry*, 47, pp. 539-614.

Ballentine, C.J., et al., (1996), "A Magnus Opus: Helium, neon, and argon isotopes in a North Sea oilfield", *Geochemica et Cosmochimica Acta*, 60(5), 831-849.

Ballentine, C.J., et al., (1991), "Rare Gas Constraints on Hydrocarbon Accumulation, Crustal Degassing and Groundwater Flow in the Pannonian Basin", *Earth and Planetary Science Letters*, 105, pp. 229-246.

Battani, A., et al., (2010), "Trinidad Mud Volcanoes: The origin of the gas", *Shale Tectonics: AAPG Bulletin Memoir*, 93, pp. 225-238.

Bell, R. J., et al., (2007), "Calibration of an in situ membrane inlet mass spectrometer for measurements of dissolved gases and volatile organics in seawater", *Environ. Sci. Technol.* 41, pp. 8123-8128.

Bosch, A., et al., (1988), "Natural Gas Association with water and oil as depicted by atmospheric noble gases: case studies from the southeastern Mediterranean Coastal Plain", *Earth and Planetary Science Letters*, 87, 338-346.

Camilli, R., et al., (2010), "Tracking Hydrocarbon Plume Transport and Biodegradation at Deepwater Horizon", *Science* 330, pp. 201-204.

Camilli. R.C., et al., (2009), "Characterizing Spatial and Temporal Variability of Dissolved Gases in Aquatic Environments with in situ Mass Spectrometry", *Environmental Science and Technology* 43(13), pp. 5014-5021.

Camilli, R., et al. (2007), "Characterizing Marine Hydrocarbons With in-Situ Mass Spectrometry", IEEE/MTS Oceans (IEEE/MTS, Vancouver, Canada, 2007), pp. 1-7.

Chung, H.M., et al., (1988), "Origin of gaseous hydrocarbons in subsurface environments: theoretical considerations of carbon isotope distribution in M. Schoell (Ed.)", *Origins of Methane in the Earth. Chem. Geol.*, 71, pp. 97-103.

Crovetto, R., et al., (1982), "Solubilities of inert gases and methane in $H_2O$ and $D_2O$ in the temperature range of 300 to 600K", *Journal of Chemical Physics* 76(2), pp. 1077-1086.

Dunn-Norman, S., et al, (2004), "Reliability of Pressure Signals in Offshore Pipeline Leak Detection", *Final Report to Dept. of the Interior*, MMS TA&R Program SOL 1435-01-00-RP-31077.

Heaton, T.H.E., et al., (1981), "'Excess air' in groundwater", *Journal of Hydrology*, 50, pp. 201-216.

Hohl, D, et al., (2010), "Energy, Environment and Climate Directorate White Paper", *DCO Energy, Environment and Climate Workshop*, pp. 1-38.

Holbrook, W.S., et al., (2003), "Thermohaline fine structure in an oceanographic front from seismic reflection profiling", *Science*, v. 301, pp. 821-824.

Huc, A., (2003), "Petroleum Geochemistry at the Dawn of the $21^{st}$ Century", *Oil & Gas Science and Technology—Rev. Ifp*, vol. 58, No. 2, pp. 233-241.

Kharaka, Y.K., et al., (1988), "The solubility of noble gases in crude oil at 25-100° C", *Applied Geochemistry*, 3, pp. 137-144.

Kinsey, J.C., et al., (2011), "Assessing the deepwater horizon oil spill with the sentry autonomous underwater vehicle", IROS'11—2011 IEEE/RSJ International Conference on Intelligent Robots and Systems: Celebrating 50 Years of Robotics. IEEE International Conference on Intelligent Robots and Systems, pp. 261-267.

Jakuba, M.V., et al., (2011), "Toward automatic classification of chemical sensor data from autonomous underwater vehicles", AIROS'11—2011 IEEE/RSJ International Conference on Intelligent Robots and Systems: Celebrating 50 Years of Robotics. IEEE International Conference on Intelligent Robots and Systems, pp. 4722-4727.

Lamontagne, R.A., et al., (2001), "Response of METS Sensor to Methane Concentrations Found on the Texas-Louisiana Shelf in the Gulf of Mexico", *Naval Research Laboratory report NRL/MR/6110*—01-8584, pp. 1-13.

Larter, S.R., et al., (1995), "Reservoir geochemistry: methods, applications and opportunities", *Geological Society of London Special Publication*, 86, pp. 5-32.

Liu, W., et al. (2007), "Ternary Geochemical-Tracing System in Natural Gas Accumulation", *Science in China Series D-Earth Sciences*, vol. 50, No. 10, pp. 1494-1503.

Makris NC, et al. (2006), "Fish Population and Behavior Revealed by Instantaneous Continental Shelf-Scale Imaging", *Science*, 311, pp. 660-663.

Mangelsdorf, K., et al., (2011), "Microbial Lipid Markers Within and Adjacent to Challenger Mound in the Belgica Carbonate Mound Province, Porcupine Basin, Offshore Ireland (IODP Expedition 307)", *Marine Geology* 282, pp. 91-101.

Narr, W.M., et al., (1984), "Origin of reservoir fractures in Little Knife Field, North Dakota", *American Association of Petroleum Geologists Bulletin*, 68, pp. 1087-1100.

Ozgul, E., (2002), "Geochemical Assessment of Gaseous Hydrocarbons: Mixing of Bacterial and Thermogenic Methane in the Deep Subsurface Petroleum System, Gulf of Mexico Continental Slope", *Thesis, Texas A&M University*, pp. 1-167.

Pinti, D.L., et al., (1995), "Noble gases in crude oils from the Paris Basin: Implications for the origin of fluids and constraints on oil-was-gas-interactions", *Geochemica et Cosmochimica Acta*, 59(16), pp. 3389-3404.

Prinzhofer, A., et al. (2003), "Gas Isotopes Tracing: An Important Tool for Hydrocarbons Exploration", *Oil & Gas Science and Technology—Rev. Ifp*, vol. 58, No. 2, pp. 299-311.

Sackett, WM, (1977), "Use of Hydrocarbon Sniffing in Offshore Exploration", *Journal of Geochemical Exploration* 7, pp. 243-254.

Smith, S.P., (1985), "Noble gas solubility in water at high temperature", *EOS Transactions of the American Geophysical Union*, 66, pp. 397.

Valentine, D.L, et al., (2010), "Asphalt Volcanoes as a Potential Source of Methane to Late Pleistocene Coastal Waters", *Nature Geoscience Letters*, DOI: 10.1038/NGEO848, pp. 345-348.

Zaikowski, A., et al., (1990), "Noble gas and methane partitioning from ground water: An aid to natural gas exploration and reservoir evaluation", *Geology*, 18, pp. 72-74.

Zartman, R.E., et al., (1961), "Helium, argon, and carbon in some natural gases", *Journal of geophysical research*, 66(1), pp. 227-306.

Zhang, Y., et al., (2011), "A peak-capture algorithm used on an autonomous underwater vehicle in the 2010 Gulf of Mexico oil spill response scientific survey", *Journal of Field Robotics*, vol. 28, No. 4, pp. 484-496.

Eiler, J.M., (2007), ""Clumped-Isotope" Geochemistry—The Study of Naturally-Occurring, Multiply-Substituted Isotopologues", *ScienceDirect Earth and Planetary Science Letters*, vol. 262, pp. 309-327.

Michel-Le Pierres, K., et al., (2010), "Radon, Helium and CO2 Measurements in Soils Overlying a Former Exploited Oilfield, Pechelbronn District, Bas-Rhin, France", *Journal of Environmental Radioactivity*, vol. 101, pp. 835-846.

\* cited by examiner

METHOD FOR DETERMINING THE LOCATION, SIZE, AND FLUID COMPOSITION OF A SUBSURFACE HYDROCARBON ACCUMULATION

CROSS REFERENCE TO RELATED APPLICATION

This application is the National Stage of International Application No. PCT/US2012/064551, that published as WO 2013/071188, filed 9 Nov. 2012, which claims the benefit of International Application No. PCT/US2012/52542, filed 27 Aug. 2012, which claims the benefit of U.S. Provisional Patent Application 61/558,822 filed 11 Nov. 2011 entitled METHOD FOR DETERMINING THE PRESENCE AND LOCATION OF A SUBSURFACE HYDROCARBON ACCUMULATION AND THE ORIGIN OF THE ASSOCIATED HYDROCARBONS, each of which is incorporated herein by reference, in its entirety, for all purposes. This application also claims the benefit of U.S. Provisional Patent Application 61/595,394 filed 6 Feb. 2012, entitled A METHOD TO DETERMINE THE LOCATION, SIZE AND IN SITU CONDITIONS IN A HYDROCARBON RESERVOIR WITH ECOLOGY, GEOCHEMISTRY, AND COLLECTIONS OF BIOMARKERS, the entirety of which is incorporated by reference herein. This application also claims the benefit of U.S. Provisional Patent Application 61/616,813 FILED 28 Mar. 2012, entitled METHOD FOR DETERMINING THE PRESENCE AND VOLUME OF A SUBSURFACE HYDROCARBON ACCUMULATION, the entirety of which is incorporated by reference herein.

FIELD OF THE DISCLOSURE

Embodiments of the present disclosure relate generally to the field of geochemistry and biology. More particularly, the present disclosure relates to systems and methods for determining the presence and estimating information, such as the location, fluid type and quality, and volume of a subsurface hydrocarbon accumulation.

BACKGROUND

This section is intended to introduce various aspects of the art, which may be associated with exemplary embodiments of the present disclosure. This discussion is believed to assist in providing a framework to facilitate a better understanding of particular aspects of the disclosed methodologies and techniques. Accordingly, it should be understood that this section should be read in this light, and not necessarily as admissions of prior art.

Hydrocarbon reserves are becoming increasingly difficult to locate and access, as the demand for energy grows globally. Typically, various components are utilized to collect measurement data and then to predict the location of potential hydrocarbon accumulations. The modeling may include factors, such as (1) the generation and expulsion of liquid and/or gaseous hydrocarbons from a source rock, (2) migration of hydrocarbons to an accumulation in a reservoir rock, (3) a trap and a seal to prevent significant leakage of hydrocarbons from the reservoir.

At present, reflection seismic is the dominant technology for the identification of hydrocarbon accumulations. This technique has been successful in identifying structures that may host hydrocarbon accumulations, and may also be utilized to image the hydrocarbon fluids within subsurface accumulations as direct hydrocarbon indicators (DHIs). However, seismic imaging of geological occurrences may be challenging in several cases where acoustic impedance contrasts that generate DHIs are greatly diminished or absent (e.g. imaging of subsurface geological occurrences at increasing depth, sub-volcanic, or sub-salt). Consequently, this technology may lack the required fidelity to provide accurate assessments of the location, volume, and fluid composition of subsurface hydrocarbon accumulations due to poor imaging of the subsurface.

Current non-seismic hydrocarbon detection technologies, such as potential field based methods like gravity or magnetics, provide coarse geologic subsurface control by sensing different physical properties of rocks, but lack the fidelity to identify hydrocarbon accumulations. Other non-seismic hydrocarbon accumulation detection technologies may include geological extrapolations of structural or stratigraphic trends that lead to exploration prospects, but cannot directly detect hydrocarbon accumulation materiality.

Hydrocarbon seepage at the sea floor or on land provides some indication of an active or working hydrocarbon system where hydrocarbons have been generated and expulsed during the thermal maturation of a source rock at depth, and have migrated via more or less complex migration pathways to the surface. Alternatively, it may be associated with migration of hydrocarbons produced during the microbial degradation of organic matter in the subsurface that may or not be associated with an accumulation. However, it is not possible using current technologies to determine whether such hydrocarbon seepages migrated directly from a source rock, from a failed trap without significant residence time within an accumulation, or from an existing hydrocarbon accumulation.

Further, the presence of non-hydrocarbon gases associated with hydrocarbon accumulations has implications for production and the economics of the accumulated hydrocarbons. Such non-hydrocarbon gases may include carbon dioxide, nitrogen, and hydrogen sulfide that were co-generated with the trapped hydrocarbons or were transported separately to the site of accumulation. There are no current direct pre-drill methods available to allow for the de-risking of non-hydrocarbon gases.

Many recent failures in hydrocarbon exploration have been associated with the inability to fully evaluate, understand, and appropriately risk the hydrocarbon system components, from source to seeps (migration, accumulation and leakage). Indeed, certain conventional technologies involve the identification and characterization of thermogenic hydrocarbons from seeps. However, there are no known tools that can directly link the geochemical composition of thermogenic hydrocarbon and/or biological species recovered from surface seeps to the size, depth, and fluid types/quality of subsurface hydrocarbon accumulations. A major advance in the ability to detect the presence, size, depth, and fluid type/quality of subsurface hydrocarbon accumulations would significantly improve hydrocarbon (HC) resource exploration in frontier and play extension settings. A method integrating existing and new biological and geochemical indicators is able to achieve this change, and integration with geological/geophysical contextual knowledge would further allow a breakthrough in opportunity identification. This invention provides a valuable, inexpensive, and rapid tool that can be used in hydrocarbon exploration at all business stage levels, from frontier exploration or extension of proven plays to high-grading prospects within proven plays.

As a result, geoscientists need to enhance techniques used for the identification of hydrocarbon accumulations. In particular, a need exists for pre-drill technologies capable of estimating the volume of subsurface hydrocarbon accumulations and technologies capable of determining the location, type (e.g. oil vs. gas) and quality (e.g. density) of the subsurface hydrocarbon accumulation. Further, a need exists to enhance techniques that identify relationships between the different data types collected for subsurface hydrocarbon accumulations.

SUMMARY

In one embodiment, a method of determining a presence, type, quality and/or volume of a subsurface hydrocarbon accumulation from a sample related thereto is described. The method comprising: obtaining sample data associated with a subsurface hydrocarbon accumulation, wherein the sample data comprises two or more of a noble gas signature of the sample, a clumped isotope signature of the sample and a ecology signature of the sample; identifying one or more relationships between the obtained two or more of the noble gas signature; the clumped isotope signature and the ecology signature, wherein the identified relationships relate to hydrocarbon accumulation materiality; and storing the identified relationships and the sample data in memory.

In one or more embodiments, the method may include other steps. For example, the method step of identifying one or more relationships may be based on one or more of a presence of a subsurface hydrocarbon accumulation, a type of hydrocarbons in the subsurface accumulation, a quality of hydrocarbons in the subsurface accumulation, a depth of hydrocarbons in the subsurface accumulation, a hydrocarbon/water volume ratio in the subsurface accumulation prior to escape to the surface, and a volume of the subsurface accumulation. Also, the method may include obtaining one or more of geologic data, biological data and geophysical data associated with a subsurface hydrocarbon accumulation; identifying one or more relationships between the obtained two or more of the noble gas signature; the clumped isotope signature and the ecology signature and the one or more of geologic data, biological data and geophysical data; and storing the identified relationships and the one or more of geologic data, biological data and geophysical data in memory. Further, the method step of identifying one or more relationships may include comparing the two or more of the noble gas signature; the clumped isotope signature and the ecology signature with a calibration dataset that comprises two or more of noble gas signatures; the clumped isotope signatures and the ecology signatures for known subsurface accumulation. The method step of identifying one or more relationships may comprise comparing the two or more of the noble gas signature; the clumped isotope signature and the ecology signature with quantitative models. In addition, the method step of identifying one or more relationships may comprise using a biogeoinformatic framework. The method may include using a calibrated dataset that may be stored in and applied through a biogeoinformatic framework.

Further, in one or more embodiments, the method may include obtaining a sample associated with a subsurface hydrocarbon accumulation; and determining the clumped isotope signature of the sample, wherein determining the clumped isotope signature comprises: determining an expected concentration of isotopologues of a hydrocarbon species from the sample; modeling, using high-level ab initio calculations, an expected temperature dependence of isotopologues present in the sample; measuring a clumped isotopic signature of the isotopologues present in the sample; comparing the clumped isotopic signature with the expected concentration of isotopologues; determining, using said comparison, whether hydrocarbons present in the sample originate directly from a source rock or whether the hydrocarbons present in the sample have escaped from a subsurface accumulation; determining the current equilibrium storage temperature of the hydrocarbon species in the subsurface accumulation prior to escape to the surface; and determining a location of the subsurface accumulation.

Further still, in one or more embodiments, the method may include obtaining a sample associated with a subsurface hydrocarbon accumulation; and characterizing the ecology signature of the sample, wherein characterizing the ecology signature may include using a first plurality of analyses to determine a community structure of an ecology of the sample; using a second plurality of analyses to determine a community function of the ecology of the sample; using the community structure and the community function to determine whether the ecology of the sample matches a characteristic ecology of a hydrocarbon system that is associated with the subsurface hydrocarbon accumulation; and when the ecology of the sample matches the characteristic ecology, identifying the sample as part of the hydrocarbon system.

Moreover, in one or more embodiments, the method may include obtaining a sample associated with a subsurface hydrocarbon accumulation; and determining the noble gas signature of the sample, wherein determining the noble gas signature comprises measuring or modeling an initial concentration of atmospheric noble gases present in formation water in contact with a seep associated with the subsurface hydrocarbon accumulation; modifying the measured/modeled initial concentration by accounting for ingrowth of radiogenic noble gases during residence time of the formation water; measuring concentrations and isotopic ratios of atmospheric noble gases and radiogenic noble gases present in the sample; comparing the measured concentrations and isotopic ratios of the atmospheric noble gases and the radiogenic noble gases present in the sample to the measured/modified modeled concentrations of the formation water for a plurality of exchange processes; determining a source of hydrocarbons present in the sample; comparing an atmospheric noble gas signature measured in the hydrocarbon phase with the measured/modified modeled concentration of the atmospheric noble gases in the formation water for the plurality of exchange processes; and determining at least one of a presence of a subsurface hydrocarbon accumulation, a type of hydrocarbons in the subsurface accumulation, a quality of hydrocarbons in the subsurface accumulation, a hydrocarbon/water volume ratio in the subsurface accumulation prior to escape to the surface, and a volume of the subsurface accumulation.

These and other features and advantages of the present disclosure will be readily apparent upon consideration of the following description in conjunction with the accompanying drawings.

BRIEF DESCRIPTION OF THE DRAWINGS

Advantages of the present techniques may become apparent upon reviewing the following detailed description and the accompanying drawings in which.

DETAILED DESCRIPTION

Figure 1:
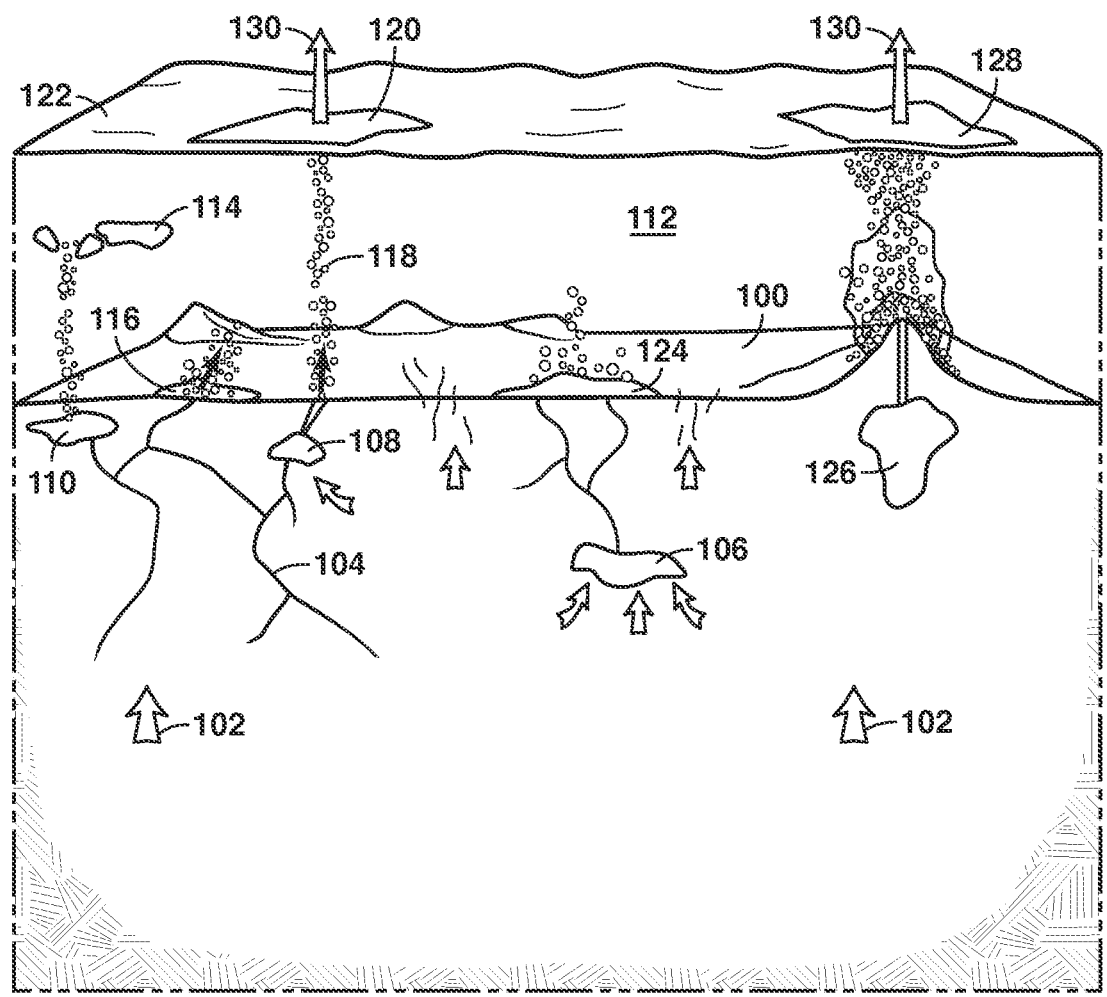
FIG. 1 is a side elevational view of a seafloor.

Various terms as used herein are defined below. To the extent a term used in a claim is not defined below, it should be given the definition persons in the pertinent art have given that term in the context in which it is used.

As used herein, "a" or "an" entity refers to one or more of that entity. As such, the terms "a" (or "an"), "one or more", and "at least one" can be used interchangeably herein unless a limit is specifically stated.

As used herein, the terms "comprising," "comprises," "comprise," "comprised," "containing," "contains," "contain," "having," "has," "have," "including," "includes," and "include" are open-ended transition terms used to transition from a subject recited before the term to one or more elements recited after the term, where the element or elements listed after the transition term are not necessarily the only elements that make up the subject.

As used herein, "exemplary" means exclusively "serving as an example, instance, or illustration." Any embodiment described herein as exemplary is not to be construed as preferred or advantageous over other embodiments.

As used herein "hydrocarbons" are generally defined as molecules formed primarily of carbon and hydrogen atoms such as oil and natural gas. Hydrocarbons may also include other elements or compounds, such as, but not limited to, halogens, metallic elements, nitrogen, oxygen, sulfur, hydrogen sulfide ($H_2S$) and carbon dioxide ($CO_2$). Hydrocarbons may be produced from hydrocarbon reservoirs through wells penetrating a hydrocarbon containing formation. Hydrocarbons derived from a hydrocarbon reservoir may include, but are not limited to, petroleum, kerogen, bitumen, pyrobitumen, asphaltenes, tars, oils, natural gas, or combinations thereof. Hydrocarbons may be located within or adjacent to mineral matrices within the earth, termed reservoirs. Matrices may include, but are not limited to, sedimentary rock, sands, silicates, carbonates, diatomites, and other porous media.

As used herein, "hydrocarbon production" or "producing hydrocarbons" refers to any activity associated with extracting hydrocarbons from a well or other opening. Hydrocarbon production normally refers to any activity conducted in or on the well after the well is completed. Accordingly, hydrocarbon production or extraction includes not only primary hydrocarbon extraction but also secondary and tertiary production techniques, such as injection of gas or liquid for increasing drive pressure, mobilizing the hydrocarbon or treating by, for example chemicals or hydraulic fracturing the wellbore to promote increased flow, well servicing, well logging, and other well and wellbore treatments.

As used herein the term "noble gases" refers to a series of chemically inert elements that exhibit similar properties. The six noble gases that occur naturally are helium (He), neon (Ne), argon (Ar), krypton (Kr), xenon (Xe) and radon (Rn). The noble gases considered in this disclosure are He, Ne, Ar, Kr and Xe.

As used herein the term "isotope" refers to one of two or more atoms with the same atomic number but with different numbers of neutrons. Each element of the noble gases has at least two isotopes. For example, helium can be present as one of two stable isotopes: $^{3}$He, which has 2 protons and 1 neutron (shown herein as $^{3}$He); and, $^{4}$He, which has 2 protons and 2 neutrons.

As used herein the term "signatures" refers to the relative abundances, concentrations and/or ratios of various elements and isotopes of a given species.

As used herein the term "formation water" refers to any water that resides within the subsurface that may be present in a reservoir rock including water in the porous media within the accumulation or immediately below but in contact with the hydrocarbon accumulation (i.e. the water leg). This may derive from a) meteoric origin, b) recharge of surface waters such as rain water or seawater that then migrates through permeable rock within the subsurface, and/or c) water trapped in the sediment during burial and remaining in place.

As used herein the term "residence time" refers to the time period that formation water has been present within the subsurface, and can be considered the age of the formation water.

As used herein the term "radiogenic" refers to generation or creation of a substance through radioactive decay of another substance. Radiogenic noble gases include $^{4}$He, $^{21}$Ne, $^{40}$Ar, $^{82}$Kr, $^{86}$Kr, $^{129}$Xe, and $^{130}$Xe and $^{136}$Xe.

As used herein the term "thermogenic" refers to hydrocarbons generated from kerogen that is currently/has in the past been subjected to high temperature and pressure.

As used herein the term "de-risk" refers to an assessment of the possibility that undesirable species such as $H_2S$, $CO_2$ are present at concentrations that would make production or refining of hydrocarbons more difficult or reduce the value of produced hydrocarbons.

As used herein, the term "computer component" refers to a computer-related entity, either hardware, firmware, software, a combination thereof, or software in execution. For example, a computer component can be, but is not limited to being, a process running on a processor, a processor, an object, an executable, a thread of execution, a program, and/or a computer. One or more computer components can reside within a process and/or thread of execution and a computer component can be localized on one computer and/or distributed between two or more computers.

As used herein, the terms "computer-readable medium" or "tangible machine-readable medium" refer to any tangible storage that participates in providing instructions to a processor for execution. Such a medium may take many forms, including but not limited to, non-volatile media, and volatile media. Non-volatile media includes, for example, NVRAM, or magnetic or optical disks. Volatile media includes dynamic memory, such as main memory. Computer-readable media may include, for example, a floppy disk, a flexible disk, hard disk, magnetic tape, or any other magnetic medium, magneto-optical medium, a CD-ROM, any other optical medium, a RAM, a PROM, and EPROM, a FLASH-EPROM, a solid state medium like a holographic memory, a memory card, or any other memory chip or cartridge, or any other physical medium from which a computer can read. When the computer-readable media is configured as a database, it is to be understood that the database may be any type of database, such as relational, hierarchical, object-oriented, and/or the like. Accordingly, exemplary embodiments of the present techniques may be considered to include a tangible storage medium or tangible distribution medium and prior art-recognized equivalents and successor media, in which the software implementations embodying the present techniques are stored.

Some portions of the detailed description which follows are presented in terms of procedures, steps, logic blocks, processing and other symbolic representations of operations on data bits within a computer memory. These descriptions and representations are the means used by those skilled in the data processing arts to most effectively convey the substance of their work to others skilled in the art. In the present application, a procedure, step, logic block, process, or the like, is conceived to be a self-consistent sequence of steps or instructions leading to a desired result. The steps are those requiring physical manipulations of physical quantities. Usually, although not necessarily, these quantities take the form of electrical or magnetic signals capable of being stored, transferred, combined, compared, and otherwise manipulated in a computer system.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present application, discussions using the terms such as "modeling", "modifying", "measuring", "comparing", "determining", "analyzing", "outputting", "displaying", "estimating", "integrating", or the like, refer to the action and processes of a computer system, or similar electronic computing device, that transforms data represented as physical (electronic) quantities within the computer system's registers and memories into other data similarly represented as physical quantities within the computer system memories or registers or other such information storage, transmission or display devices. Example methods may be better appreciated with reference to flow diagrams.

While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks. While the figures illustrate various serially occurring actions, it is to be appreciated that various actions could occur concurrently, substantially in parallel, and/or at substantially different points in time.

In the following section, specific embodiments of the disclosed methodologies and techniques are described in connection with disclosed aspects and techniques. However, to the extent that the following description is specific to a particular aspect, technique, or a particular use, this is intended to be for exemplary purposes only and is not limited to the disclosed aspects and techniques described below, but rather include all alternatives, modifications, and equivalents falling within the scope of the appended claims.

This present disclosure involves a system and method for determining the presence and estimating information, such as volume, location, type and quality about a subsurface hydrocarbon accumulation. This method and system provides an enhanced technique that may be a valuable tool for use in hydrocarbon exploration at various maturity levels, from frontier exploration to extension of proven plays to high-grading prospects within proven plays. In particular, the present techniques involve the use of three independent technologies: clumped isotope geochemistry, noble gas geochemistry, and ecology, which are combined and integrated with other traditional techniques as a workflow to enhance hydrocarbon accumulation identification and recovery. These three methods may provide information about the volume, depth and fluid type (oil vs. gas) and quality of subsurface hydrocarbon accumulations to be determined from the sampling and analysis of hydrocarbons seeps (e.g., offshore and/or onshore). That is, the method may integrate existing and new biological and geochemical indicators to provide insights in opportunity identification. In addition, the integration of these biological and geochemical indicators with geological/geophysical contextual knowledge should further provide enhancements to hydrocarbon accumulation opportunity identification. Further, relationships between these data may also be utilized to further enhance the process.

In one embodiment, the present techniques involve the integration of one or more of microbial genomics; noble gas geochemistry and clumped isotope geochemistry of hydrocarbon phases. This integrated workflow may be utilized to determine and/or estimate the presence and information, such as volume, depth, type, quality, and location of the subsurface hydrocarbon accumulation.

The microbial genomics may be utilized to provide information on the metabolic processes of subsurface microbial communities linked with those microbes sampled within sea-bottom seeps. This microbial genomics information provides an indication as to the presence of a subsurface accumulation and provides an estimation of its location (e.g., depth) based on biologic temperature ranges. This aspect relies upon the transport microbes from deep to shallow habitats to a hydrocarbon seep from subsurface hydrocarbon accumulations. This process may explain, for example, the presence of "displaced" thermophiles (microbes that live in high temperature environments) in arctic environments where crude oil is potentially degraded by anaerobic microbes, thus supporting a connection to a deeper hydrocarbon/sediment source. Different areas of hydrocarbon seepage may have different microbial anomalies relative to normal marine conditions, depending on subsurface reservoir conditions. An understanding of the metabolic processes of subsurface microbial communities linked with those microbes sampled within seabottom seeps should allow the presence of a subsurface accumulation to be detected and allow an estimation of its location (depth) based on biologic temperature ranges.

As an example, one embodiment may include a method of identifying a hydrocarbon system. In this method, a sample from an area of interest is obtained. Then, a first plurality of analyses is used to determine a community structure of an ecology of the sample and a second plurality of analyses is used to determine a community function of the ecology of the sample. The community structure and the community function are used to determine whether the ecology of the sample matches a characteristic ecology of a hydrocarbon system. When the ecology of the sample matches the characteristic ecology, the sample is identified as part of the hydrocarbon system. This aspect is further described in U.S. Patent No. 61/595,394, which is incorporated herein in its entirety.

With regard to the noble gas geochemistry, the noble gases (He, Ne, Ar, Kr, Xe) are conservative elements that do not generally participate in chemical reactions. The concentrations of noble gases in oil, gas, and water are based on the combined influence of their solubilities, which are a function of pressure, temperature, and fluid composition (P-T-X) that prevailed during dissolution or exsolution, interaction and mixing with other fluids, and the ingrowth of noble gases from the radioactive decay of crustal minerals. If the water PTX conditions in contact with a subsurface hydrocarbon accumulation can be estimated or measured, the hydrocarbon accumulation size can be estimated or calculated based on the solubility partitioning of noble gases between water and hydrocarbons. An atmospherically uncontaminated hydrocarbon seep sample analyzed for noble gases along with estimated water PTX conditions, should allow an accumulation size (hydrocarbon/water ratio) to be estimated.

As an example, one embodiment may include a method for determining the presence, type, quality and/or volume of a subsurface hydrocarbon accumulation from a sample related thereto. An initial concentration of atmospheric noble gases present in formation water in contact with the subsurface hydrocarbon accumulation is measured or modeled. The modeled initial concentration is modified by accounting for ingrowth of radiogenic noble gases during residence time of the formation water. A sample related to the subsurface hydrocarbon accumulation is obtained. Concentrations and isotopic ratios of noble gases present in the sample are measured. The measured concentrations and isotopic ratios of the atmospheric noble gases and the radiogenic noble gases present in the sample are compared to the measured/modified modeled concentrations of the formation water for a plurality of exchange processes. A source of hydrocarbons present in the sample is determined. An atmospheric noble gas signature measured in the hydrocarbon phase is compared with the measured/modified modeled concentration of the atmospheric noble gases in the formation water for the plurality of exchange processes. At least one of a presence of a subsurface hydrocarbon accumulation, a type of hydrocarbons in the subsurface accumulation, a quality of hydrocarbons in the subsurface accumulation, a hydrocarbon/water volume ratio in the subsurface accumulation prior to escape to the surface, and a volume of the subsurface accumulation is determined.

In another aspect, a method is disclosed for determining a presence, type, quality and volume of a subsurface hydrocarbon accumulation based on analysis of a sample related thereto. The sample is analyzed to determine a geochemical signature of the sample. An initial concentration of atmospheric noble gases present in formation water in contact with the subsurface hydrocarbon accumulation is determined. Ingrowth of radiogenic noble gases is modeled to modify the initial concentration for given formation water residence times. A residence time of the formation water is determined. An extent of interaction with a hydrocarbon phase is determined. The origin of the sample is determined. At least one of a type, quality and hydrocarbon/water volume ratio when the origin of the sample is a hydrocarbon accumulation is determined. From the hydrocarbon/water volume ratio, the volume of the hydrocarbon accumulation is determined.

In another aspect, a method is disclosed for determining a presence, type, quality and volume of a subsurface hydrocarbon accumulation from a hydrocarbon sample thereof. An initial concentration of atmospheric noble gases present alongside a hydrocarbon species is determined. A range of expected concentrations of atmospheric and radiogenic noble gases present in the sample is modeled for a range of residence times and for various extents of interaction between formation water and a hydrocarbon phase. Concentrations and isotopic ratios of noble gases present in the sample are measured. The measured noble gas concentrations are compared with the modeled range of expected concentrations of atmospheric and radiogenic noble gases. Using the comparison it is determined whether the hydrocarbons present in the sample have escaped from the subsurface accumulation. From the measured noble gas concentrations and the modeled range of expected concentrations of atmospheric and radiogenic noble gases, the presence, type and quality of hydrocarbons in the subsurface accumulation and the hydrocarbon/formation water volume ratio of the subsurface accumulation are estimated. The estimated presence, type and quality of hydrocarbons in the subsurface accumulation and the hydrocarbon/formation water volume ratio of the subsurface accumulation are integrated with seismic reflection constraints on a volume of the hydrocarbon accumulation and a volume of water present in the hydrocarbon accumulation, thereby determining the volume of hydrocarbons present in the subsurface accumulation.

In still another aspect, a system is disclosed for determining a presence, type, quality and volume of a subsurface hydrocarbon accumulation from a hydrocarbon sample thereof. The system includes a processor and a tangible, machine-readable storage medium that stores machine-readable instructions for execution by the processor. The machine-readable instructions include code for determining expected concentrations of noble gases present in formation waters, code for modeling one or more exchange and fractionation processes in the expected concentrations of noble gases present in the sample, code for measuring concentrations of noble gases present in the sample, code for comparing the measured concentrations of noble gases with the modeled concentrations of noble gases in the formation waters, code for determining, using said comparison, the presence, type and quality of hydrocarbons present in the subsurface, and code for determining whether hydrocarbons present in the sample originate directly from a source rock or whether the hydrocarbons present in the sample have escaped from a subsurface accumulation.

In still another aspect, a computer program product having computer executable logic recorded on a tangible, machine readable medium, the computer program product comprising: code for determining expected concentrations of noble gases present in formation waters, code for modeling one or more exchange and fractionation processes in the expected concentrations of noble gases present in a hydrocarbon sample taken from a hydrocarbon seep, code for measuring concentrations of noble gases present in the hydrocarbon sample, code for comparing the measured concentrations of noble gases with the modeled concentrations of noble gases in the formation waters, code for determining, using said comparison, a presence, a type and a quality of hydrocarbons present in the hydrocarbon sample, and code for determining whether hydrocarbons present in the hydrocarbon sample originate directly from a source rock or whether the hydrocarbons present in the sample have escaped from a subsurface accumulation.

In yet another aspect, a method of producing hydrocarbons, comprising: determining a presence, type, quality and/or volume of a subsurface hydrocarbon accumulation from a hydrocarbon sample thereof, wherein the determining includes modeling an initial concentration of atmospheric noble gases present in formation water in contact with a subsurface hydrocarbon accumulation, modifying the modeled initial concentration by accounting for ingrowth of radiogenic noble gases during residence time of the formation water, obtaining a hydrocarbon sample, measuring concentrations and isotopic ratios of atmospheric, mantle derived and radiogenic noble gases present in the hydrocarbon sample, comparing the measured concentrations and isotopic ratios of the atmospheric noble gases and the radiogenic noble gases present in the hydrocarbon sample to the modified modeled concentrations of the formation water for a plurality of exchange processes, determining a source of hydrocarbons present in the hydrocarbon sample, comparing an atmospheric noble gas signature measured in the hydrocarbon phase with the modified modeled concentration of the atmospheric noble gases in the formation water for a plurality of exchange processes, determining at least one of a presence of a subsurface hydrocarbon accumulation, a type of hydrocarbons in the subsurface accumulation, a quality of hydrocarbons in the subsurface accumulation, a hydrocarbon/water volume ratio in the subsurface accumulation prior to escape to the surface, and a volume of the subsurface accumulation; and producing hydrocarbons using at least one of the determined type, quality, volume ratio, and volume of the subsurface accumulation. This aspect is further described in U.S. Patent No. 61/616,813, which is incorporated herein in its entirety.

A hydrocarbon compound contains atoms of carbon and hydrogen, and will be present as a natural stable isotope of carbon ($^{12}C$, $^{13}C$) or hydrogen ($^1H$, or $^2H$ often termed deuterium or D). $^{12}C$ forms 98.93% of the carbon on Earth, while $^{13}C$ forms the remaining 1.07%. Similarly, the isotopic abundance of $^1H$ on earth is 99.985% while $^2H$ has an abundance of 0.015%. Isotopologues are compounds with the same chemical formula, but differ in their molecular mass based on which isotopes are present in the molecule (e.g. $^{13}C^1H_3D$ or $^{12}C^1H_4$). Clumped isotopes are isotopologues in which two or more rare isotopes are present in close proximity (i.e., isotopic 'clumps'), and for which the molecular ordering of isotopes is as important as their total abundance. These rare species have distinctive thermodynamic stabilities and rates of reaction with specific fractionations during diffusion and mixing, and are far more diverse than the singly-substituted species that are the focus of established branches of isotope geochemistry. Common volatile hydrocarbons have large numbers of stable isotopologues (e.g., methane has 10; ethane has 21; propane has 36). Measurements of a single gas species could, in principle, yield two or more mutually independent thermometers that could indicate the "residence" temperature of hydrocarbons within a subsurface accumulation, in effect determining the depth location of a potential exploration target from a seep sample.

As an example, one embodiment may include a method of determining a presence and location of a subsurface hydrocarbon accumulation from a sample of naturally occurring substance. According to the method, an expected concentration of isotopologues of a hydrocarbon species is determined. An expected temperature dependence of isotopologues present in the sample is modeled using high-level ab initio calculations. A signature of the isotopologues present in the sample is measured. The signature is compared with the expected concentration of isotopologues. Using the comparison, it is determined whether hydrocarbons present in the sample originate directly from a source rock or whether the hydrocarbons present in the sample have escaped from a subsurface accumulation. The current equilibrium storage temperature of the hydrocarbon species in the subsurface accumulation prior to escape to the surface is determined. A location of the subsurface accumulation is determined.

Also according to disclosed methodologies and techniques, a method of determining a presence and location of a subsurface hydrocarbon accumulation is provided. According to the method, a hydrocarbon sample is obtained from a seep. The hydrocarbon sample is analyzed to determine its geochemical signature. The analyzing includes measuring a distribution of isotopologues for a hydrocarbon species present in the hydrocarbon sample. A stochastic distribution of the isotopologues for the hydrocarbon species is determined. A deviation of the measured distribution of isotopologues from the stochastic distribution of the isotopologues for the hydrocarbon species is determined. The origin of the hydrocarbon sample is determined. A storage temperature of the hydrocarbon species is determined when the origin of the hydrocarbon sample is a hydrocarbon accumulation. From the storage temperature, the location of the hydrocarbon accumulation is determined.

According to methodologies and techniques disclosed herein, a method is provided for determining a presence of a subsurface hydrocarbon accumulation from a sample of naturally occurring substance. According to the method, an expected concentration of isotopologues of a hydrocarbon species is determined. An expected temperature dependence of isotopologues present in the sample is modeled using high-level ab initio calculations. A clumped isotopic signature of the isotopologues present in the sample is measured. The clumped isotopic signature is compared with the expected concentration of isotopologues. It is determined, using the comparison, whether the hydrocarbons present in the sample have escaped from a subsurface accumulation, thereby determining a presence of the subsurface accumulation.

According to disclosed methodologies and techniques, A computer system is provided that is configured to determine a presence and location of a subsurface hydrocarbon accumulation from a sample of naturally occurring substance. The computer system includes a processor and a tangible, machine-readable storage medium that stores machine-readable instructions for execution by the processor. The machine-readable instructions include: code for determining an expected concentration of isotopologues of a hydrocarbon species; code for modeling, using high-level ab initio calculations, an expected temperature dependence of isotopologues present in the sample; code for measuring a clumped isotopic signature of the isotopologues present in the sample; code for comparing the clumped isotopic signature with the expected concentration of isotopologues; and code for determining, using said comparison, whether hydrocarbons present in the sample originate directly from a source rock or whether the hydrocarbons present in the sample have escaped from a subsurface accumulation.

According to still more disclosed methodologies and techniques, a method of determining a presence and location of a subsurface hydrocarbon accumulation and the origin of associated hydrocarbons collected from a surface seep is provided. According to the method, molecular modeling is integrated to determine the expected concentration of isotopologues from a hydrocarbon species of interest. A concentration of the isotopologues of the hydrocarbon species of interest is measured. Statistical regression analysis is conducted to converge on a temperature-dependent equilibrium constant and an isotopic signature unique to the absolute concentrations measured for multiple co-existing isotopologues. For the hydrocarbons collected from the surface seep, at least one of storage temperature, a source facies, and thermal maturity of source rock associated therewith is determined. This aspect is further described in U.S. Patent No. 61/558,822, which is incorporated herein in its entirety.

Beneficially, this integrated workflow provides a non-seismic based technology that is capable of determining hydrocarbon accumulation materiality. Further, this process provides the ability to detect the presence, volume, depth, and fluid type/quality of subsurface hydrocarbon accumulations, which is useful in hydrocarbon (HC) resource exploration in frontier and play extension settings. The process provides a useful technique that is inexpensive relative to current technologies and may efficiently be utilized in hydrocarbon exploration at the different business stage levels, from frontier exploration or extension of proven plays to high-grading prospects within proven plays. As a result, this process provides geoscientists with an enhanced identification technique for hydrocarbon accumulations, while having a greater confidence in the identified hydrocarbon accumulations.

Furthermore, in the absence of suitable reflection seismic interpretations on hydrocarbon volumes or direct measurements of hydrocarbon saturation using geophysical logging tools, the present techniques may be utilized to provide a pre-drill technology capable of estimating the volume of subsurface hydrocarbon accumulations and/or capable of determining the depth, fluid type (oil vs. gas), quality (e.g. density and composition), and location of particular targets or prospective subsurface hydrocarbon accumulations. This functionality does not appear to be provided by conventional technologies. Various aspects of the present techniques are described further in FIGS. 1 to 4.

FIG. 1 is a diagram illustrating the numerous subsurface sources and migration pathways of hydrocarbons present at or escaping from seeps on the ocean floor 100. Hydrocarbons 102 generated at source rock (not shown) migrate upward through faults and fractures 104. The migrating hydrocarbons may be trapped in reservoir rock and form a hydrocarbon accumulation, such as a gas 106, oil and gas 108, or a gas hydrate accumulation 110. Hydrocarbons seeping from the gas hydrate accumulation may dissolve into methane in the ocean 112 as shown at 114, or may remain as a gas hydrate on the ocean floor 100 as shown at 116. Alternatively, oil or gas from oil/gas reservoir 108 may seep into the ocean, as shown at 118, and form an oil slick 120 on the ocean surface 122. A bacterial mat 124 may form at a gas seep location, leaking from gas reservoir 106, and may generate biogenic hydrocarbon gases while degrading thermogenic wet gas. Still another process of hydrocarbon seepage is via a mud volcano 126, which can form an oil slick 128 on the ocean surface. Oil slicks 120 and 128 or methane gas 130 emitted therefrom are signs of hydrocarbon seepage that are, in turn, signs of possible subsurface hydrocarbon accumulation. The signatures measured from each of these seeps may be analyzed according to disclosed methodologies and techniques herein to discriminate between the different origins of hydrocarbons encountered at these seeps. In particular, methodologies and techniques disclosed herein may discriminate between hydrocarbons that have migrated directly to the surface without encountering a trap within which they can be accumulated (e.g., a first source) and hydrocarbons that have leaked from a subsurface accumulation (e.g., a second source). If the presence and volume of such a hydrocarbon accumulation can be identified, it is possible the hydrocarbons from such an accumulation can be extracted.

Figure 2:
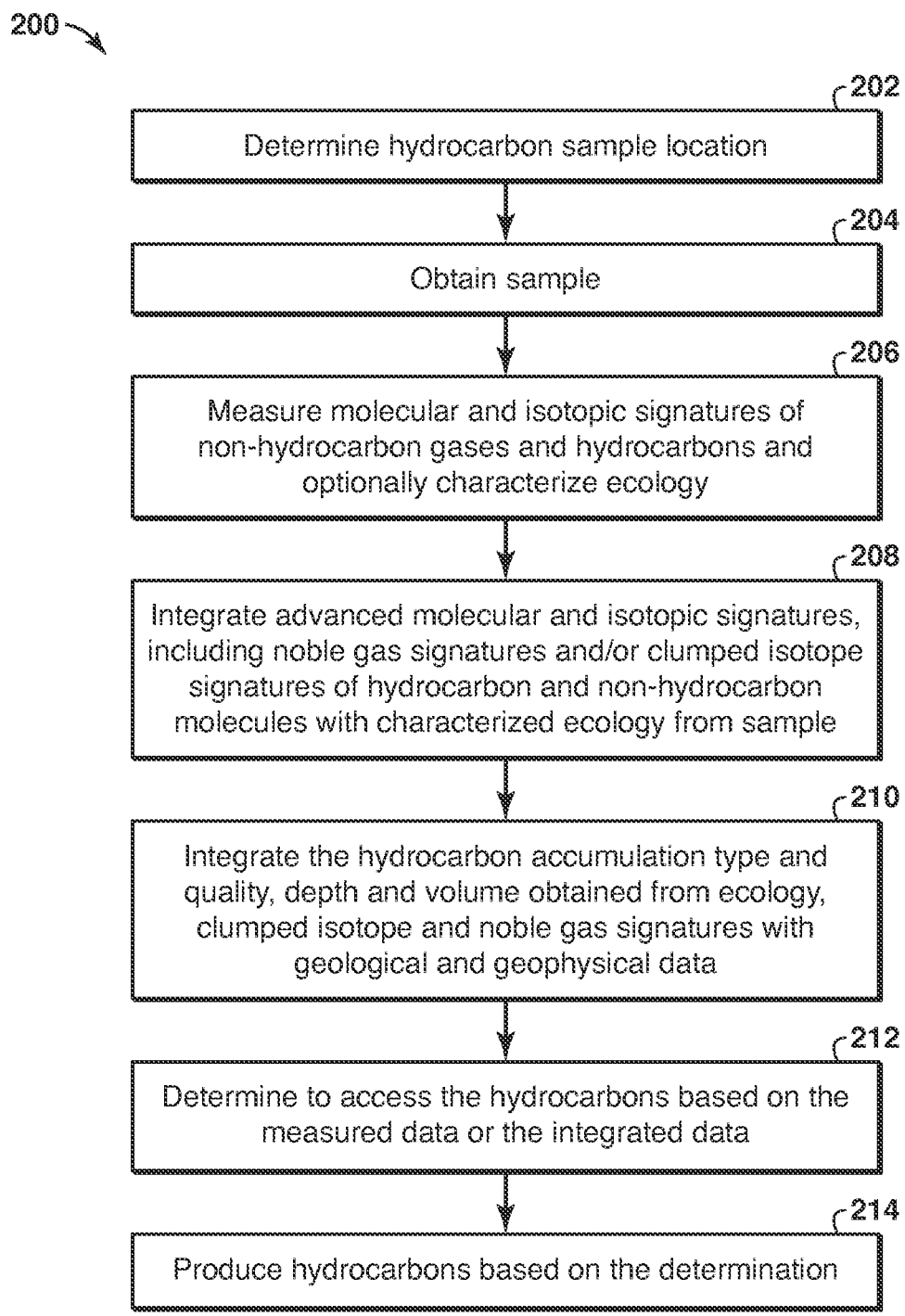
FIG. 2 is a flow diagram of a method for determining information about a hydrocarbon accumulation in accordance with an embodiment of the present techniques.

FIG. 2 is a flow diagram of a method for determining information about a hydrocarbon accumulation in accordance with an embodiment of the present techniques. The flow diagram 200 depicts a method for determining from a seep sample the depth and/or fluid type and quality (e.g. gas vs. oil, API gravity of oil) and/or volume of a subsurface hydrocarbon accumulation. The flow diagram 200 includes a sample obtaining stage, which includes blocks 202 and 204, followed by an analysis stage, which includes blocks 206, 208, 210, and followed by a hydrocarbon capture stage, which includes blocks 212 and 214.

The sample obtaining stage, which includes blocks 202 and 204, may be utilized to determine the location of the samples and obtain the samples. At block 202, hydrocarbon sample may be located. The location of the hydrocarbon sample may be based on a known seep location or determining a seep location through known techniques. Then, at block 204, one or more samples are obtained from the hydrocarbon sample location. If the hydrocarbon location is a seep, the sampling of seep locations may include (i) confirming the presence of hydrocarbons (e.g., biogenic, thermogenic, abiogenic) at the seep location and (ii) conducting advanced biological and geochemical analysis after appropriate sampling. The sampling methods used to collect the samples of interest may include gravity or piston drop core sampling, the use of manned submersibles, autonomous underwater vehicles (AUV) or remotely operated vehicles (ROV) with coring sampling devices, and gas sampling apparatus (including pinch of valves and sombreros). Sampling may also include collection of surface sediments surrounding the seep location and collection of fluids from within the seep conduit. A sample can comprise (i) any surface sample, such as a sediment sample taken from the seafloor or a sample of seeped fluids, (ii) any sample taken from the water column above a seep location, or (iii) any sample taken from within the seep conduits below the surface. Identification of the presence of hydrocarbons may be determined by standard geochemical analysis. This may include but is not restricted to maximum fluorescence intensity and standard molecular geochemistry techniques such as gas chromatography (GC). For biology samples, appropriate preservation should be taken, as is known in the art. Similarly, gases and/or oils samples that are subjected to clumped isotope and noble gas analysis may be collected using funnels or inserted into seep conduit connected to sampling cylinders.

After the sample obtaining stage, an analysis stage, which includes blocks 206, 208, 210, may be utilized to further analyze the samples. At block 206, the molecular and isotopic signatures of non-hydrocarbon gases (e.g., $H_2S$, $CO_2$, $N_2$) and hydrocarbons are measured and the ecology may be characterized. In one embodiment, these measurements may include noble gas signatures and at least one or more of clumped isotope signatures the ecology. The ecology may be characterized via DNA, RNA, lipid analysis. This measurement may include the analysis of noble gas signatures (He, Ne, Ar, Kr and Xe) and the isotopologue or clumped isotope signature of both non-hydrocarbon and hydrocarbon molecules (in gases, water, or oils). Isotopologues are molecules that differ only in their isotopic composition. Clumped isotopes are isotopologues that contain two or more rare isotopes. The sample of interest may comprise water, oil, natural gas, sediments or other type of rock, or fluids present in sediments, rocks, water or air. Measurement of the abundance of each noble gas isotope can be conducted following standard extraction techniques using mass spectrometry. Measurement of the abundance of each clumped isotope or isotopologue can be conducted using multiple techniques, such as mass spectrometry and/or laser-based spectroscopy. The ecology of samples (e.g., sediment, seawater, seeped fluids and the like) can be characterized through a number of different techniques. These may include but are not restricted to deoxyribonucleic acid (DNA) analysis, ribonucleic acid (RNA) analysis, (meta) genomics, (meta) proteomics, (meta) transcriptomics, lipid analysis, and culture-based methods. The analysis may include both (semi) quantitative (e.g., qPCR (quantitative polymerase chain reaction), next-generation sequencing) and qualitative assessments (e.g., sequencing, microscopy, phenotype tests). Standard molecular analysis is conducted to characterize the organic signature of hydrocarbons extracted from the sample. This may include gas chromatography-mass spectrometry (GC/MS), GC/GC/MS, liquid chromatography. Inorganic analysis of samples may also be conducted. This may include but is not restricted to inductively coupled plasma mass spectrometry (ICP-MS) and ICP-optical emission spectroscopy. Gas chemistry analysis may also be conducted and may include isotope ratio—mass spectrometry and GC.

At block 208, the information obtained from the advanced molecular and isotopic signatures, including noble gas signatures and clumped isotope signatures of hydrocarbon and non-hydrocarbon molecules, and characterized ecology of the samples is integrated with standard molecular analysis (as defined above). The integration of advanced molecular and isotopic signatures may include noble gas signatures and clumped isotope signatures of hydrocarbon and non-hydrocarbon molecules with characterized ecology from sample, which may also be integrated with conventional geochemical data and interpret. This integrated data is then interpreted. This interpretation involves determining the presence, type and quality of hydrocarbons and/or depth of a hydrocarbon accumulation and/or volume of a hydrocarbon accumulation. As an example, the noble gases may be utilized to determine hydrocarbon accumulation volume, hydrocarbon type and oil quality is provided in a U.S. Patent No. 61/616,813. As natural gases and oils are initially devoid of noble gases, the addition of these through interaction with formation water provides information about the samples. The impact of this interaction on isotopic ratios and absolute concentrations of noble gases present in the hydrocarbon phase is a function of three variables: (i) the initial concentration and isotopic signature of noble gases in the water phase, (ii) the solubility of noble gases in water and oil (solubility of noble gases in oil is controlled by oil quality), and (iii) the ratio of the volumes of oil/water, gas/water or gas/oil/water.

The initial concentration of noble gases in the water phase prior to interaction with any hydrocarbons can be accurately measured or estimated. Noble gases dissolve in water during recharge from meteoric waters or at the air/water boundary for seawater. This initial signature is therefore dominated by atmospheric noble gases, namely $^{20}$Ne, $^{36}$Ar, $^{84}$Kr and $^{132}$Xe. The amount of noble gases that dissolve into the water phase obeys Henry's Law, which states that the amount of noble gases dissolved in water is proportional to the partial pressure of the noble gases in the atmosphere (which varies as a function of altitude for meteoric water recharge). The Henry's constant is directly related to the salinity of the water phase and the ambient temperature during the transfer of noble gases to the water. Formation waters recharged from meteoric waters at the air/soil interface may have an additional component of atmospheric derived noble gases from that which is expected purely from equilibrium, "excess air". These influences may be subject to adjustments (e.g., correction schemes, such as those noted in Aeschbach-Hertig et al., 2000, for example). See, e.g., Aeschbach-Hertig, W., Peeters, F., Beyerle, U., Kipfer, R. Palaeotemperature reconstruction from noble gases in ground water taking into account equilibrium with entrapped air. Nature, 405, 1040-1044, 2000. The resulting noble gas signature is therefore lie between air-saturated water (ASW), air-saturated seawater (ASS) and air-saturated brine (ASB) for any given temperature. Radiogenic noble gases are then introduced following recharge through radioactive decay of minerals within the subsurface. The concentration of the radiogenic noble gases typically increases with increasing formation water residence time (or age). This evolving noble gas signature in the water phase is changed as a result of mixing and interaction with other fluids.

The solubilities of noble gases in water have been determined for a range of different temperatures, as is known in the art (e.g., Crovetto et al., 1982; Smith, 1985). See, e.g., Smith, S. P. Noble gas solubilities in water at high temperature. EOS Transactions of the American Geophysical Union, 66, 397, 1985 and Crovetto, R., Fernandez-Prini, R., Japas, M. L. Solubilities of inert gases and methane in $H_2O$ and $D_2O$ in the temperature range of 300 to 600K, Journal of Chemical Physics 76(2), 1077-1086, 1982. Similarly, the measured solubility of noble gases in oil increases with decreasing oil density (Kharaka and Specht, 1988). See, e.g., Kharaka, Y. K. and Specht, D. K. The solubility of noble gases in crude oil at 25-100° C. Applied Geochemistry, 3, 137-144, 1988. The exchange of atmospheric noble gases between formation water and both the oil and/or gaseous hydrocarbon phase can occur through various processes, and the extent of fractionation induced by each of these processes gives rise to different signatures in the different phases. These processes can be modeled and may comprise equilibrium solubility, Rayleigh style fractionation and gas stripping. The exchange of noble gases between oil and water may result in the oil phase developing an enrichment in the heavy noble gases (Kr and Xe), and an associated depletion in the light noble gases (He and Ne) relative to the water phase. This is because of the greater solubility of the heavier noble gases in oil than in water. In contrast, the interaction of a gas phase with water may result in the gas phase becoming relatively enriched in the lighter noble gases and depleted in the heavy noble gases relative to a water phase. The magnitude of this fractionation may change depending upon the exchange process involved and on the density of the oil phase Assuming that a subsurface signature is preserved during migration to the surface, the phases that interacted (e.g. oil-water, gas-water or gas-oil-water) with a seeped hydrocarbon by measuring the concentration of noble gases in the hydrocarbon sample may be determined. The noble gases provide a conservative tracer of the hydrocarbon type present within the subsurface (oil vs. gas). Knowledge of the solubility of noble gases as a function of oil density provide further information about the estimate of the oil quality when the hydrocarbon present is determined to be oil. Finally, given that two of the three variables that control the exchange of noble gases between water and hydrocarbons are known or can be modeled, the hydrocarbon/water volume ratio within a subsurface hydrocarbon accumulation can be determined. From this it is possible to quantitatively predict the volume of hydrocarbon present within a subsurface accumulation.

In addition to the utilization of noble gases to determine hydrocarbon accumulation volume, hydrocarbon type and oil quality, clumped isotope geochemistry may be utilized to determine the depth of a hydrocarbon accumulation. As an example, U.S. Patent No. 61/558,822 describes a process for determining the clumped isotope signature of any molecule. The clumped isotope signature of any molecule is a function of (i) temperature-independent randomly populated processes (e.g., stochastic distribution) and (ii) thermal equilibrium isotopic exchange. The latter process is controlled or dependent on the surrounding temperature. The stochastic distribution of any isotopologue can be determined from the bulk isotope signatures of the species from which it derives. For example, determining the stochastic distribution of isotopologues for methane requires knowledge of the $^{13}C$ and D signatures of methane. The isotopic signature of hydrocarbon gases that are stored in a subsurface accumulation or that are present at seeps may reflect the isotopic signature of the gas generated from the source rock. As such, this signature may be concomitantly determined during the characterization of the hydrocarbons present at a seep and substituted directly in to the calculation of the stochastic distribution. There may be occasions, however, when the isotopic signature of gases is altered by processes like mixing with biogenic gas. In such instances, correction schemes known in the art may be relied upon, such as Chung et al., (1988). See Chung, H. M., Gormly, J. R., and Squires, R. M. *Origin of Gaseous Hydrocarbons In Subsurface Environments*. Theoretical Considerations of Carbon Isotope Distribution. Chemical Geology 71, 97-103, 1988. The correction scheme may be used to deconvolve such contributions and reach the initial primary isotope signature that should be used in the calculation of the stochastic distribution.

The expected increased abundance, or enrichment, of any given isotopologue or clumped isotope can be modeled or empirically determined for any given temperature. By measuring the clumped isotope and isotopologue signatures of a given molecule, and through knowledge of the stochastic distribution, the enrichment of the measured concentrations relative to the stochastic distribution can be used to determine the temperature in the subsurface from which this molecule is derived.

Hydrocarbons that derive from a subsurface accumulation may retain a clumped isotope signature that reflects the temperature at which the hydrocarbons were stored in the subsurface. This non-kinetic control on the isotopic exchange reactions in isotopologues of hydrocarbons that originate from a subsurface accumulation arises as a result of the inherently long residence times of hydrocarbons in the subsurface. Through application of a suitable geothermal gradient to the storage temperature derived from the clumped isotope signature, the location (depth) within the subsurface that seep associated hydrocarbon accumulations reside may be estimated.

As an example, the microbial ecology and biomarker signature of hydrocarbon seeps may be used to determine the depth of a hydrocarbon accumulation and/or the hydrocarbon accumulation volume and/or the hydrocarbon type and oil quality, as described in U.S. Patent No. 61/595,394. Ecology is the study of interactions between living organisms and the non-living surrounding environment. Microbial ecology refers to the ecology of small organisms like bacteria and archaea. Ecology includes biotic parameters like community composition (e.g., which organisms are present), community function (e.g., what are those organisms doing.), organism behavior, organism quantity and metabolite production. Additionally, ecology includes abiotic parameters like pH, temperature, pressure and aqueous concentrations of different chemical species. All or some of these parameters may be measured to describe the ecology of a hydrocarbon seep. Seeps that are connected to hydrocarbon accumulations may have different ecologies than seeps that are not connected to hydrocarbon accumulations.

Microbial ecology involves using genomics and culture based techniques to describe the community composition. (meta) genomics, (meta) transcriptomics, (meta) proteomics and lipid measurements can be combined with chemical measurements to determine the community function. Changes in temperature drive changes in community structure and function. Changes in hydrocarbon type and volume present in the accumulation change community structure and function. If a seep is connected to a hydrocarbon accumulation, these ecological differences may be reflected in samples acquired from the seep.

The sediment and fluid samples from in and around a hydrocarbon seep may be collected and appropriately preserved. Changes in the ecology of these samples may reflect the conditions of the subsurface accumulations feeding the seeps. Samples from a seep not connected to a hydrocarbon accumulation may not contain ecological parameters associated with a deep hot hydrocarbon environment.

Then, at block 210, the hydrocarbon accumulation type and quality, depth and volume obtained from the ecology (e.g., microbial ecology), clumped isotope and noble gas signatures and other standard molecular analysis may be integrated with geological and geophysical data obtained from conventional exploration or prospect assessment technologies to confirm accumulation materiality. Such technologies may include reflection seismic, high resolution seismic imaging, acoustic, basin modeling, and/or probabilistic or statistical assessments. This may include determining the location within the subsurface (both depth and lateral) that a hydrocarbon accumulation resides. It may also include confirmation of hydrocarbon accumulation volume, type and quality.

One method of integrating these different sources of data to assess hydrocarbon materiality is through the use of a biogeoinformatics. The biogeoinformatics (e.g., biogeoinformatics framework), which is described further in FIGS. 3A and 3B, may include storing information about the geochemical signatures along with other information, such as biological and geology, for example, to determine or identify relationships between calibration data and the measured data from the samples. Alternatively, another method of integrating these different sources of data to assess hydrocarbon accumulation materiality is to calibrate the individual techniques to provide indicators of a hydrocarbon accumulation depth, volume, fluid type and/or quality. This calibration approach can be conducted empirically by comparing noble gas, clumped isotope or microbial ecology signatures to hydrocarbon accumulations with known depth, pressure, temperature, volume, fluid type and quality. Data collected from a sample of interest from a seep can then be compared to the calibrated dataset and integrated with the location of interest geophysical and geological data to determine subsurface hydrocarbon accumulation materiality. Yet another method of integrating these different sources of data from a sample of interest to assess hydrocarbon accumulation materiality utilizes the sensitivity of noble gas, clumped isotope and microbial ecology signatures to geological and physical processes. As a still yet another example, the data may be integrated by combining the previously cited method for the quantitative models of noble gas and clumped isotope sensitivities to hydrocarbon accumulation materiality with a bioinformatics approach to the microbial ecology data. Then, the analysis of seep sample from a location of interest for noble gas, clumped isotope and microbial ecology signatures may provide information on the presence, depth, volume, type and/or quality of at least one potential subsurface hydrocarbon accumulation. This approach may then be integrated with the available geophysical/geological data for the specific location of interest to identify a subsurface hydrocarbon accumulation.

At block 212, a determination is made whether to access hydrocarbons from the accumulation based on the measured data or the integrated data as provided through biogeoinformatics or the like. The determination may include analyzing the measured data for one or more of the hydrocarbon accumulation type, quality, depth and volume obtained from the ecology (e.g., microbial ecology), clumped isotope and noble gas signatures and/or this data integrated with the geological and geophysical data.

Then, hydrocarbons may be produced from the hydrocarbon accumulation based on the determination, as shown in block 214. The production of the hydrocarbons may involve drilling a well to provide access to the hydrocarbon accumulation. Further, the production may include installing a production facility is configured to monitor and produce hydrocarbons from the production intervals that provide access to the subsurface formation. The production facility may include one or more units to process and manage the flow of production fluids, such as hydrocarbons and/or water, from the formation. To access the production intervals, the production facility may be coupled to a tree and various control valves via a control umbilical, production tubing for passing fluids from the tree to the production facility, control tubing for hydraulic or electrical devices, and a control cable for communicating with other devices within the wellbore.

As noted above, the integrating of the different sources of data to assess hydrocarbon materiality may be performed in a variety of manners. One method of integration is through the use of a biogeoinformatics. Bioinformatics is the science of storing and analyzing biological data. Modern DNA sequencing technology generates massive amounts of data supported by observed and other measured information. It is infeasible to store and analyze this data without the use of computers. Modern computer networks are used to store and query these data so that multivariate statistical techniques such as principle coordinate analysis that may be used to identify and describe patterns and relationships within these datasets. Geoinformatics or geographic information science uses similar computational techniques to store and investigate geographical, geological, geophysical and geochemical data. Techniques from bioinformatics and geoinformatics may be combined in order to effectively use the geochemical and microbiological data collected in this workflow.

Figure 3A:
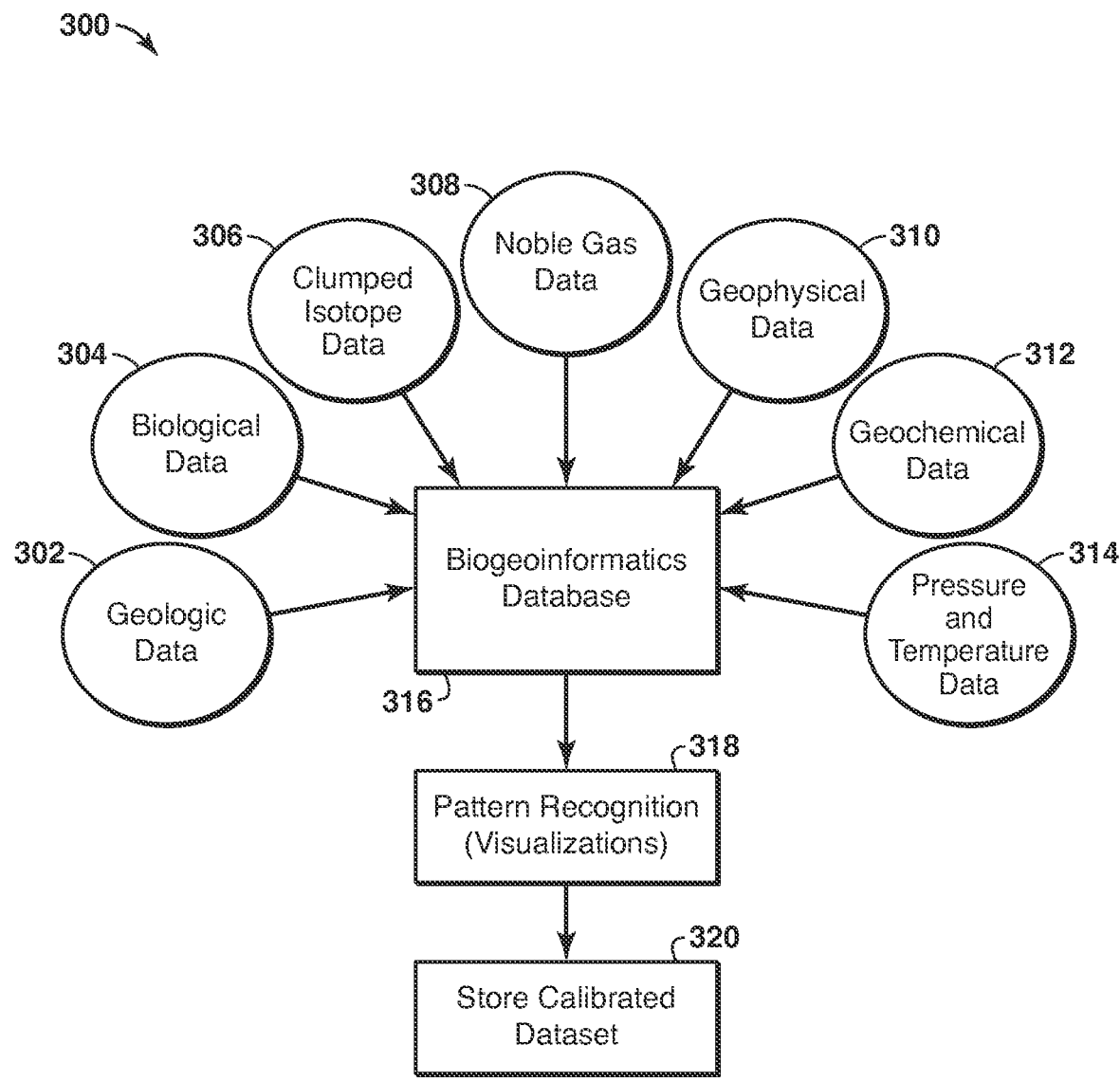
FIGS. 3A and 3B are flow diagrams for integrating the information about a hydrocarbon accumulation in accordance with an embodiment of the present techniques.

As an example, FIG. 3A is a flow diagram 300 for integrating the information about a hydrocarbon accumulation in accordance with an embodiment of the present techniques. In this flow diagram 300, an integrated biogeoinformatic database 316 may be constructed to store and query the following types of data: clumped isotope data 306, biological data 304 (e.g., microbiological data), noble gas data 308, geophysical data 310, geochemical data 312, pressure and temperature data 314 and geologic data 302. Geophysical data 310 may include, but is not limited to; seismic data, gravity measurements and/or electromagnetic data. Geochemical data 312 may include, but is not limited to, dissolved concentrations of inorganic ions and organic species, isotopic measurements, molecular compositions of oils and gasses, and characterizations of fluid inclusions. Geologic data 302 may include, but is not limited to, information about geologic structures and faults, mineralogical data, lithologic data, stratigraphic data and paleontological data. The noble gas data 308 may include signature of the elements and their isotopes, as noted above, while the clumped isotope data 306 may include a signature of the deviation from a stochastic distribution, which are also noted above.

Biological Data 304 may include nucleic acid (i.e., DNA and RNA) and protein sequences obtained directly from environmental samples (e.g., seawater, seep sample, reservoir fluids). These sequences may be obtained from a variety of sequencing platforms, including, but are not limited to, 1st generation (e.g., Sanger), PCR-based next-generation (e.g., 454 Roche, Illumina, etc.), and 3rd generation (single molecule sequencing such as HeliScope, PacBio, etc.) sequencing technologies as well as gas and liquid chromatography coupled with mass-spectrometry. Biological data may also include quantitative and semi-quantitative measures obtained from assays such as quantitative PCR (qPCR), sequencing, protein assays (e.g., western blot); as well as qualitative assessments such as those obtained from observations in nature or in the laboratory (e.g., shape or color of an organism, response of an organisms to a stimulus such as temperature or pressure).

Finally, the pressure and temperature data 314 may include the pressure and/or temperature measurements from in-situ (e.g. within the reservoir) locations using one or more sensors, such as a down hole pressure transducers and thermistors, for example. This pressure and/or temperature data may be used to calibrate the sensitivity of other parameters, such as ecology, noble gas or clumped isotope signatures to the environmental conditions.

As an example, biogeoinformatic processing is first applied to a comprehensive data set to identify patterns or relationships between subsurface accumulation materiality and geochemical and biological tracer responses (e.g., clumped isotopes, ecology, noble gases). Responses from a sample of interest where limited data is available can then be compared to calibrated datasets to identify similarities or patterns between the sample of interest and the calibrated data sets. This comparison provides additional information to provide a mechanism for the interpretation of subsurface hydrocarbon accumulation materiality from a sample of interests geochemical and biological response or signature.

All of these diverse data types may be collected into a single biogeoinformatic database 316 where they can be queried using a variety of methods. As shown in block 318, pattern recognition may be utilized to query the biogeoinformatic database 316. The pattern recognition techniques may include algorithms that can be combined with statistical descriptions of the data to find relationships between known hydrocarbon accumulations and measured indicators of the size, depth, pressure, temperature and location of these accumulations. Once these relationships have been described they can be used to explore for additional hydrocarbons. The relationships may be stored in a model as a reservoir characterization, as shown in block 320.

Alternatively, as noted above, another method of integrating these different sources of data to assess hydrocarbon accumulation materiality is to calibrate the individual techniques to provide indicators of a hydrocarbon accumulation depth, volume, fluid type and/or quality. This calibration approach can be conducted empirically by comparing noble gas, clumped isotope or microbial ecology signatures to hydrocarbon accumulations with known depth, pressure, temperature, volume, fluid type and quality. Data collected from a sample of interest, such as from a seep, can then be compared to the calibrated dataset and integrated with the location of interest geophysical and geological data to determine subsurface hydrocarbon accumulation materiality.

As an example, empirical calibration can be conducted when samples from subsurface accumulations are available within the region of interest. These samples are characterized for their noble gas, clumped isotope and microbial ecology signatures as per block 206 of FIG. 2. These signatures are then calibrated to the measured subsurface accumulation materiality from which the sample derives (e.g., accumulation depth, pressure, temperature, hydrocarbon volume). A sample taken from a seep at a specific location of interest can then be characterized for the noble gas and at least one or more of the clumped isotope and microbial ecology signatures. These signatures can then be compared to the empirical calibration for the region of interest to determine any potential subsurface hydrocarbon accumulation materiality. Then, the data integrated with the available geophysical/geological data for the specific location of interest to identify a subsurface hydrocarbon accumulation.

Another method of integrating these different sources of data from a sample of interest to assess hydrocarbon accumulation materiality utilizes the sensitivity of noble gas, clumped isotope and microbial ecology signatures to geological and physical processes. As an example, the noble gas, clumped isotope and microbial ecology signatures from a sample of interest can be compared to quantitative models developed through an understanding of noble gas solubility, partitioning processes, and ecological preferences for particular temperature and/or pressure regimes. Through the comparison of modeled sensitivities and measured signatures, the potential subsurface hydrocarbon accumulation materiality may be determined from a sample of interest. This data is then integrated with the available geophysical/geological data for the specific location of interest to identify a subsurface hydrocarbon accumulation.

Yet another example may be developed through combining the previously cited method above for the quantitative models for noble gas and clumped isotope sensitivities to hydrocarbon accumulation materiality with a bioinformatics approach to the microbial ecology data. In this approach, analysis of a sample, such as from a seep, from a location of interest for noble gas, clumped isotope and microbial ecology signatures will provide information on the presence, depth, volume, type and/or quality of at least one potential subsurface hydrocarbon accumulation. This is then integrated with the limited geophysical/geological data available for the specific location of interest to identify a subsurface hydrocarbon accumulation.

Figure 3B:
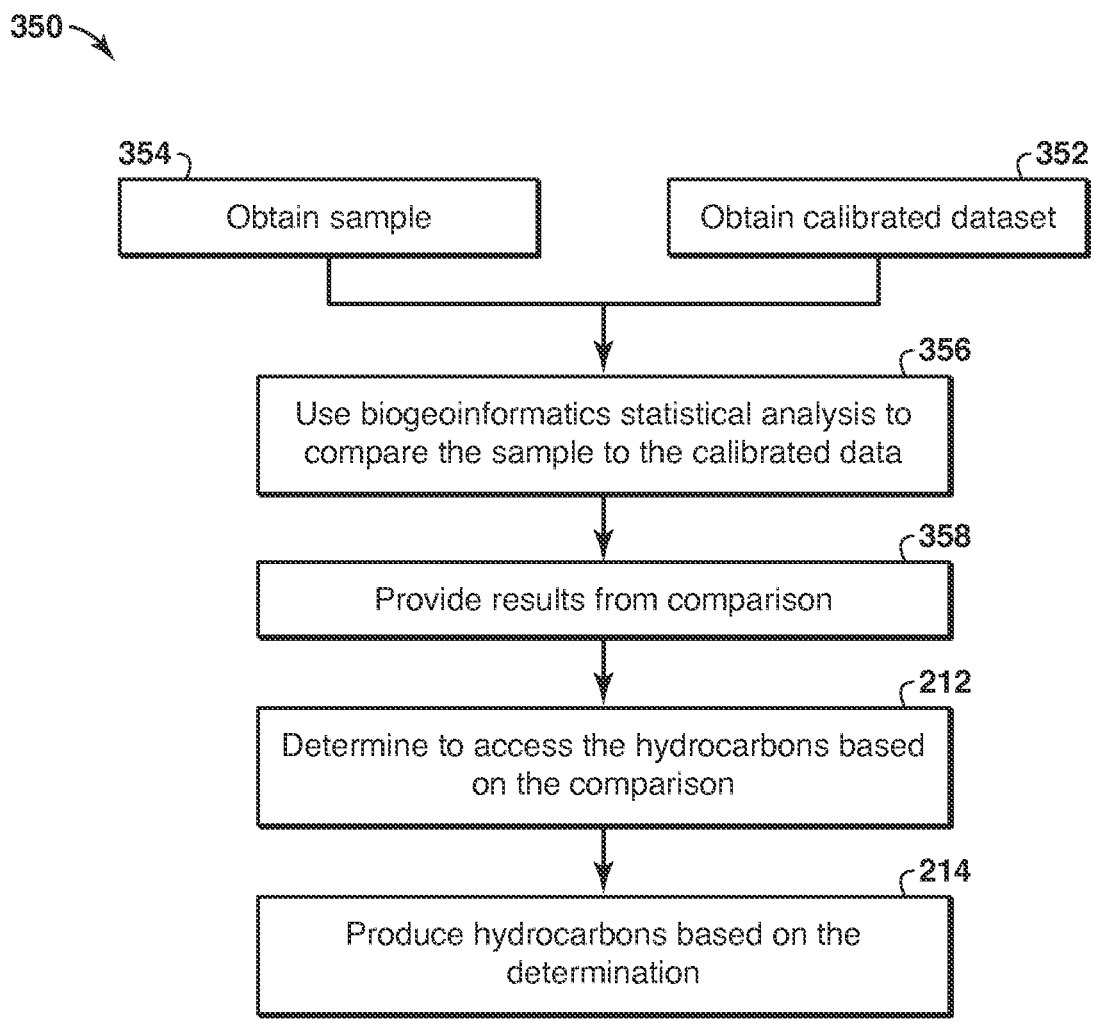

With the calibrated dataset, measured samples may be compared to known data to enhance the process. As an example, FIG. 3B is a flow diagram 350 for integrating the calibrated dataset with a measured sample. In this flow diagram 350, a sample is obtained, as noted in block 352. The sample may be analyzed to determine include the clumped isotope signature, noble gas signature, ecology signature, biological data and other geochemical data. Also, a calibrated dataset is obtained, as shown in block 354. The calibrated dataset includes data from various sources, which is associated with depth, type, quality, volume and location of known subsurface hydrocarbon accumulations. The calibrated dataset may include clumped isotope data, noble gas data, and ecology data and may also include geophysical data, other geochemical data, pressure and temperature data, biological and geologic data.

At block 356, the sample data may be compared with the calibrated dataset via biogeoinformatics statistical analysis to determine relationships between the sample data and the calibrated dataset. Then, the results of the comparison may be provided to a user, as shown in block 358. The user may use the results to estimate the location depth, type, quality, volume and location of subsurface hydrocarbon accumulation. Following this a determination is made whether to access hydrocarbons from the accumulation based on the comparison, as noted in block 212, and hydrocarbons may be produced, as noted in block 214. Blocks 212 and 214 may be performed in a manner noted above in FIG. 2.

In one or more embodiments, a variety of sample sources may be characterized for ecology and advanced molecular and isotopic signatures, which may enhance development, improvement, and optimization of the tools for exploration. These samples may include, produced fluids from operating facilities, sediment and seawater samples near and at certain distances from a seep. The data generated may establish markers of interest (e.g., markers for hydrocarbon quality or reservoir temperature) and lessen uncertainties associated with exploring unknown reservoirs.

Figure 4:
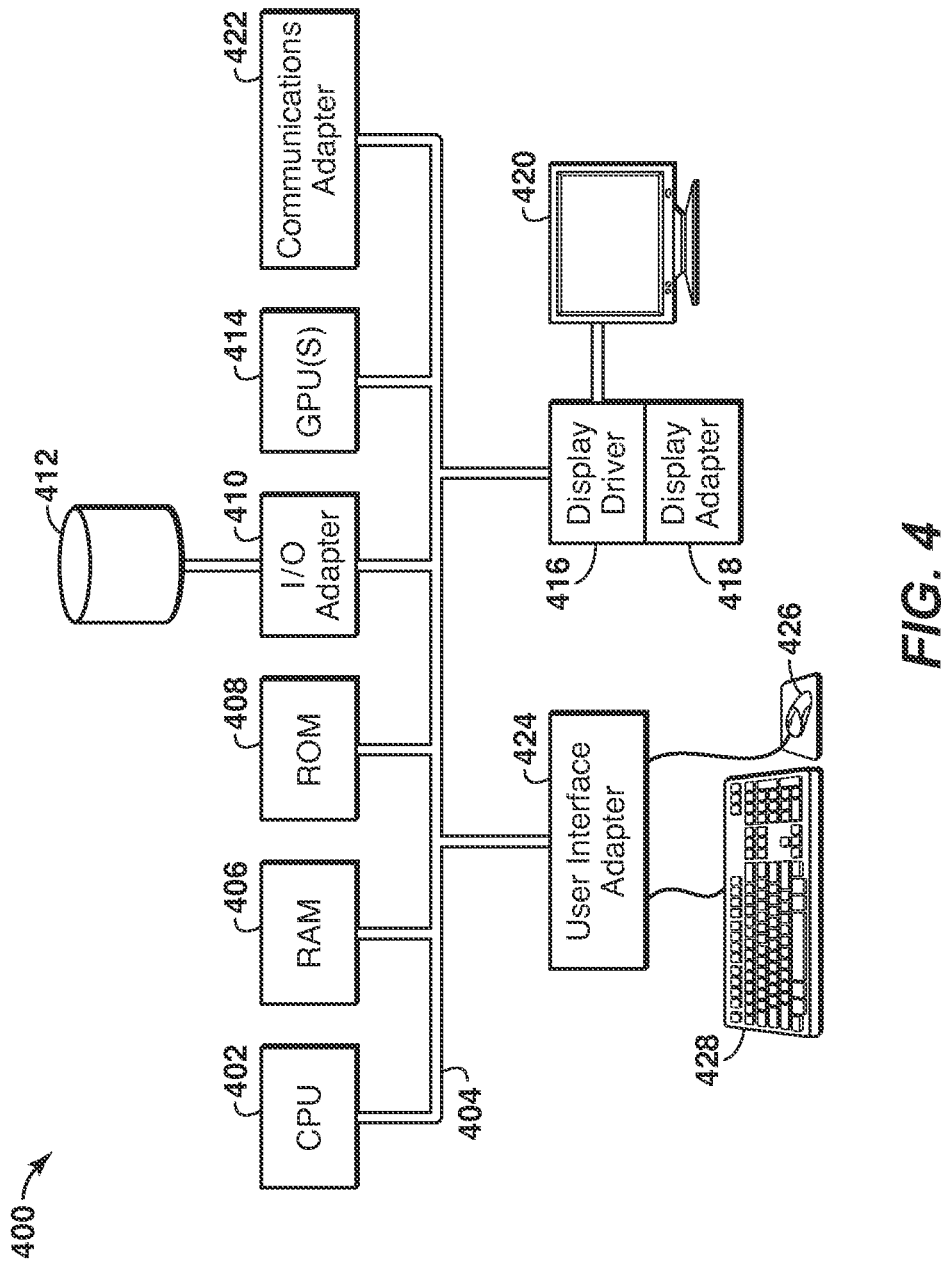
FIG. 4 is a block diagram of a computer system according to disclosed methodologies and techniques.

FIG. 4 is a block diagram of a computer system 400 that may be used to perform any of the methods disclosed herein. A central processing unit (CPU) 402 is coupled to system bus 404. The CPU 402 may be any general-purpose CPU, although other types of architectures of CPU 402 (or other components of exemplary system 400) may be used as long as CPU 402 (and other components of system 400) supports the inventive operations as described herein. The CPU 402 may execute the various logical instructions according to disclosed aspects and methodologies. For example, the CPU 402 may execute machine-level instructions for performing processing according to aspects and methodologies disclosed herein.

The computer system 400 may also include computer components such as a random access memory (RAM) 406, which may be SRAM, DRAM, SDRAM, or the like. The computer system 400 may also include read-only memory (ROM) 408, which may be PROM, EPROM, EEPROM, or the like. RAM 406 and ROM 408 hold user and system data and programs, as is known in the art. The computer system 400 may also include an input/output (I/O) adapter 410, a communications adapter 422, a user interface adapter 424, and a display adapter 418. The I/O adapter 410, the user interface adapter 424, and/or communications adapter 422 may, in certain aspects and techniques, enable a user to interact with computer system 400 to input information.

The I/O adapter 410 preferably connects a storage device(s) 412, such as one or more of hard drive, compact disc (CD) drive, floppy disk drive, tape drive, etc. to computer system 400. The storage device(s) may be used when RAM 406 is insufficient for the memory requirements associated with storing data for operations of embodiments of the present techniques. The data storage of the computer system 400 may be used for storing information and/or other data used or generated as disclosed herein. The communications adapter 422 may couple the computer system 400 to a network (not shown), which may enable information to be input to and/or output from system 400 via the network (for example, a wide-area network, a local-area network, a wireless network, any combination of the foregoing). User interface adapter 424 couples user input devices, such as a keyboard 428, a pointing device 426, and the like, to computer system 400. The display adapter 418 is driven by the CPU 402 to control, through a display driver 416, the display on a display device 420. Information and/or representations of one or more 2D canvases and one or more 3D windows may be displayed, according to disclosed aspects and methodologies.

The architecture of system 400 may be varied as desired. For example, any suitable processor-based device may be used, including without limitation personal computers, laptop computers, computer workstations, and multi-processor servers. Moreover, embodiments may be implemented on application specific integrated circuits (ASICs) or very large scale integrated (VLSI) circuits. In fact, persons of ordinary skill in the art may use any number of suitable structures capable of executing logical operations according to the embodiments.

In one or more embodiments, the method of FIG. 2, 3A or 3B may be implemented in machine-readable logic, set of instructions or code that, when executed, performs a method to determine and/or estimate the presence and information, such as depth, type, quality, volume and location of the subsurface hydrocarbon accumulation from a sample related thereto. The code may be used or executed with a computing system such as computing system 400.

In other embodiments, the method noted above may be utilized to perform hydrocarbon production activities, such as extracting hydrocarbons from a subsurface formation, region, or reservoir. A method of producing hydrocarbons from subsurface reservoir may include predicting the presence and/or volume of hydrocarbons in the subsurface region is predicted according to methodologies and techniques disclosed herein. Then, the hydrocarbons accumulation may be accessed by drilling a wellbore to the subsurface location. The drilling of the wellbore may include known techniques and the use of oil drilling equipment. Once the well is completed, hydrocarbon production is conducted to remove and/or otherwise produce hydrocarbons from the subsurface region. Other hydrocarbon management activities may be performed according to known principles.

Illustrative, non-exclusive examples of methods and products according to the present disclosure are presented in the following non-enumerated paragraphs. It is within the scope of the present disclosure that an individual step of a method recited herein, including in the following enumerated paragraphs, may additionally or alternatively be referred to as a "step for" performing the recited action.

One or more exemplary embodiments are described below in the following paragraphs.

1. A method of determining a presence, type, quality and/or volume of a subsurface hydrocarbon accumulation from a sample related thereto, the method comprising:
obtaining seep sample data associated with a subsurface hydrocarbon accumulation, wherein the sample data comprises two or more of a noble gas signature of the sample, a clumped isotope signature of the sample and a ecology signature of the sample;
identifying one or more relationships between the obtained two or more of the noble gas signature; the clumped isotope signature and the ecology signature, wherein the identified relationships relate to hydrocarbon accumulation materiality; and
storing the identified relationships and the sample data in memory.

2. The method of paragraph 1, wherein the identifying one or more relationships is based on one or more of a presence of a subsurface hydrocarbon accumulation, a type of hydrocarbons in the subsurface accumulation, a quality of hydrocarbons in the subsurface accumulation, a depth of hydrocarbons in the subsurface accumulation, a hydrocarbon/water volume ratio in the subsurface accumulation prior to escape to the surface, and a volume of the subsurface accumulation.

3. The method of any one of paragraphs 1 to 2, further comprising:
obtaining one or more of geologic data, biological data and geophysical data associated with a subsurface hydrocarbon accumulation;
identifying one or more relationships between the obtained two or more of the noble gas signature; the clumped isotope signature and the ecology signature and the one or more of geologic data, biological data and geophysical data; and
storing the identified relationships and the one or more of geologic data, biological data and geophysical data in memory.

4. The method of any one of paragraphs 1 to 3, wherein identifying one or more relationships comprises comparing the two or more of the noble gas signature; the clumped isotope signature and the ecology signature with a calibration dataset that comprises two or more of noble gas signatures; the clumped isotope signatures and the ecology signatures for known subsurface accumulation.

5. The method of any one of paragraphs 1 to 3, wherein identifying one or more relationships comprises comparing the two or more of the noble gas signature; the clumped isotope signature and the ecology signature with quantitative models.

6. The method of any one of paragraphs 1 to 3, wherein identifying one or more relationships comprises using a biogeoinformatic framework.

7. The method of any one of paragraphs 1 to 6, comprising obtaining a seep sample associated with a subsurface hydrocarbon accumulation; and determining the noble gas signature of the sample, wherein determining the noble gas signature comprises: measuring or modeling an initial concentration of atmospheric noble gases present in formation water in contact with the subsurface hydrocarbon accumulation; modifying the measured/modeled initial concentration by accounting for ingrowth of radiogenic noble gases during residence time of the formation water; measuring concentrations and isotopic ratios of atmospheric noble gases and radiogenic noble gases present in the sample; comparing the measured concentrations and isotopic ratios of the atmospheric noble gases and the radiogenic noble gases present in the sample to the measured/modified modeled concentrations of the formation water for a plurality of exchange processes; determining a source of hydrocarbons present in the sample; comparing an atmospheric noble gas signature measured in the hydrocarbon phase with the measured/modified modeled concentration of the atmospheric noble gases in the formation water for the plurality of exchange processes; and determining at least one of a presence of a subsurface hydrocarbon accumulation, a type of hydrocarbons in the subsurface accumulation, a quality of hydrocarbons in the subsurface accumulation, a hydrocarbon/water volume ratio in the subsurface accumulation prior to escape to the surface, and a volume of the subsurface accumulation.

8. The method of paragraph 7, wherein the plurality of exchange processes include at least one of equilibrium solubility laws calibrated to reflect conditions in the subsurface accumulation, Rayleigh-style fractionation to represent the de-gassing of an oil phase, and gas stripping to represent enrichment in a gas phase.

8A. The method of paragraph 8, wherein the conditions include at least one of reservoir temperature, pressure, formation water salinity and oil density.

9. The method of paragraph 7, wherein the noble gases include at least one of helium (He), neon (Ne), argon (Ar), krypton (Kr), and xenon (Xe).

10. The method of paragraph 7, wherein the isotopic ratios include a ratio of Kr to Ar, which may include the ratio of Kr to Ar as a ratio of $^{84}Kr/^{36}Ar$.

11. The method of paragraph 7, wherein the isotopic ratios include a ratio of Xe to Ar, which may include the ratio of Xe to Ar as a ratio of $^{132}Xe/^{36}Ar$.

12. The method of paragraph 7, wherein the isotopic ratios include a ratio of Ne to Ar, which may include the ratio of krypton to argon is a ratio of $^{20}Ne/^{36}Ar$.

13. The method of paragraph 7, wherein determining a source of hydrocarbons present in the sample comprises determining whether hydrocarbons present in the sample originate directly from a source rock, or have escaped from a subsurface accumulation.

14. The method of paragraph 7, further comprising producing hydrocarbons based on at least one of the determined presence, type, quality, hydrocarbon/water volume ratio, and the volume of the subsurface accumulation.

15. The method of paragraph 7, wherein the initial concentration is modeled to reflect a salinity of the fluid and temperature of exchange during recharge/exchange with atmosphere.

16. The method of paragraph 7, wherein the sample comprises one of water, oil, natural gas, sediments, rock, fluids present in sediments, fluids from rock pores, and fluids trapped in fluid inclusions.

17. The method of paragraph 7, further comprising characterizing non-hydrocarbon gas risk associated with the subsurface hydrocarbon accumulation.

18. The method of any one of paragraphs 1 to 6, wherein determining the noble gas signature comprises: analyzing the seep sample to determine a geochemical signature of the sample; determining an initial concentration of atmospheric noble gases present in formation water in contact with the subsurface hydrocarbon accumulation; modeling ingrowth of radiogenic noble gases to modify the initial concentration for given formation water residence times; determining a residence time of the formation water; determining an extent of interaction with a hydrocarbon phase; determining the origin of the sample; determining at least one of a presence, type, quality and hydrocarbon/water volume ratio when the origin of the sample is a hydrocarbon accumulation; and from the hydrocarbon/water volume ratio, determining the volume of the hydrocarbon accumulation.

19. The method of paragraph 16, wherein the noble gases include at least one of helium (He), neon (Ne), argon (Ar), krypton (Kr), and xenon (Xe).

20. The method of paragraph 18, wherein the isotopic ratios include at least one of $^{84}Kr/^{36}Ar$, $^{132}Xe/^{36}Ar$, and $^{20}Ne/^{36}Ar$.

21. The method of paragraph 18, wherein determining the origin of the hydrocarbon sample comprises determining whether hydrocarbons present in the hydrocarbon sample originate directly from a source rock, or have escaped from a subsurface accumulation.

22. The method of any one of paragraphs 1 to 6, comprising obtaining a sample associated with a subsurface hydrocarbon accumulation; and determining the noble gas signature of the sample, wherein determining the noble gas signature comprises: determining an initial concentration of atmospheric noble gases present alongside a hydrocarbon species; modeling a range of expected concentrations of atmospheric and radiogenic noble gases present in the sample for a range of residence times and for various extents of interaction between formation water and a hydrocarbon phase; measuring concentrations and isotopic ratios of noble gases present in the sample; comparing the measured noble gas concentrations with the modeled range of expected concentrations of atmospheric and radiogenic noble gases; determining, using the comparison, whether the hydrocarbons present in the sample have escaped from the subsurface accumulation; estimating, from the measured noble gas concentrations and the modeled range of expected concentrations of atmospheric and radiogenic noble gases, the presence, type and quality of hydrocarbons in the subsurface accumulation and the hydrocarbon/formation water volume ratio of the subsurface accumulation; and integrating the estimated presence, type and quality of hydrocarbons in the subsurface accumulation and the hydrocarbon/formation water volume ratio of the subsurface accumulation with seismic reflection constraints on a volume of the hydrocarbon accumulation and a volume of water present in the hydrocarbon accumulation, thereby determining the volume of hydrocarbons present in the subsurface accumulation.

23. The method of paragraph 22, wherein the noble gases include at least one of helium (He), neon (Ne), argon (Ar), krypton (Kr), and xenon (Xe).

24. The method of paragraph 22, wherein the isotopic ratios include at least one of $^{84}Kr/^{36}Ar$, $^{132}Xe/^{36}Ar$, and $^{20}Ne/^{36}Ar$.

25. The method of any one of paragraphs 1 to 6, comprising obtaining a sample associated with a subsurface hydrocarbon accumulation; and determining the noble gas signature of the sample, wherein determining the noble gas signature comprises: utilizing a processor and a tangible, machine-readable storage medium that stores machine-readable instructions for execution by the processor, wherein the machine-readable instructions include code for determining expected concentrations of noble gases present in formation waters, code for modeling one or more exchange and fractionation processes in the expected concentrations of noble gases present in the sample, code for measuring concentrations of noble gases present in the sample, code for comparing the measured concentrations of noble gases with the modeled concentrations of noble gases in the formation waters, code for determining, using said comparison, the presence, type and quality of hydrocarbons present in the subsurface, and code for determining whether hydrocarbons present in the sample originate directly from a source rock or whether the hydrocarbons present in the seep sample have escaped from a subsurface accumulation.

26. The method of any one of paragraphs 1 to 6, comprising obtaining a sample associated with a subsurface hydrocarbon accumulation; and determining the noble gas signature of the sample, wherein determining the noble gas signature comprises: utilizing a computer program product having computer executable logic recorded on a tangible, machine readable medium, the computer program product comprising: code for determining expected concentrations of noble gases present in formation waters, code for modeling one or more exchange and fractionation processes in the expected concentrations of noble gases present in a hydrocarbon sample taken from a hydrocarbon seep, code for measuring concentrations of noble gases present in the hydrocarbon seep sample, code for comparing the measured concentrations of noble gases with the modeled concentrations of noble gases in the formation waters, code for determining, using said comparison, a presence, type and a quality of hydrocarbons present in the hydrocarbon sample, and code for determining whether hydrocarbons present in the hydrocarbon sample originate directly from a source rock or whether the hydrocarbons present in the sample have escaped from a subsurface accumulation.

27. The method of any one of paragraphs 1 to 26, comprising obtaining a sample associated with a subsurface hydrocarbon accumulation; and determining the clumped isotope signature of the sample wherein determining the clumped isotope signature of the sample comprises: determining an expected concentration of isotopologues of a hydrocarbon species; modeling, using high-level ab initio calculations, an expected temperature dependence of isotopologues present in the sample; measuring a clumped isotopic signature of the isotopologues present in the sample; comparing the clumped isotopic signature with the expected concentration of isotopologues; determining, using said comparison, whether hydrocarbons present in the sample originate directly from a source rock or whether the hydrocarbons present in the sample have escaped from a subsurface accumulation; determining the current equilibrium storage temperature of the hydrocarbon species in the subsurface accumulation prior to escape to the surface; and determining a location of the subsurface accumulation.

28. The method of paragraph 27, wherein determining an expected concentration of isotopologues includes determining a stochastic distribution of isotopologues of the hydrocarbon species for a given bulk isotopic signature for the species.

29. The method of paragraph 28, further comprising: where the given bulk isotopic signature of the hydrocarbon species has been altered from secondary isotope exchange processes or from mixing, applying a correction scheme to arrive at an initial primary isotopic signature representative of what was produced from the source rock.

30. The method of paragraph 27, wherein the location comprises a depth.

31. The method of paragraph 29, wherein determining a location includes applying a thermal gradient to an equilibrium storage temperature of the subsurface accumulation.

32. The method of paragraph 27, further comprising determining a precise location of the subsurface hydrocarbon accumulation using a geophysical imaging technique.

33. The method of paragraph 36, wherein the geophysical imaging technique is seismic reflection.

34. The method of any one of paragraphs 1 to 26, comprising obtaining a sample associated with a subsurface hydrocarbon accumulation; and determining the clumped isotope signature of the sample, wherein determining the clumped isotope signature of the sample comprises: obtaining a hydrocarbon sample from a seep; analyzing the hydrocarbon sample to determine its geochemical signature, said analyzing including measuring a distribution of isotopologues for a hydrocarbon species present in the hydrocarbon sample; determining a stochastic distribution of the isotopologues for the hydrocarbon species; determining a deviation of the measured distribution of isotopologues from the stochastic distribution of the isotopologues for the hydrocarbon species; determining an origin of the hydrocarbon sample; determining a storage temperature of the hydrocarbon species when the origin of the hydrocarbon sample is a hydrocarbon accumulation; and from the storage temperature, determining the location of the hydrocarbon accumulation.

35. The method of any one of paragraphs 1 to 34, obtaining a sample associated with a subsurface hydrocarbon accumulation; and characterizing the ecology signature of the sample, wherein characterizing the ecology signature of the sample comprises: using a first plurality of analyses to determine a community structure of an ecology of the sample; using a second plurality of analyses to determine a community function of the ecology of the sample; using the community structure and the community function to determine whether the ecology of the sample matches a characteristic ecology of a hydrocarbon system; and when the ecology of the sample matches the characteristic ecology, identifying the sample as part of a hydrocarbon system associated with the subsurface hydrocarbon accumulation.

35A. The method of paragraph 35, wherein the sample is obtained from sediment near a hydrocarbon seep.

36. The method of paragraph 35, wherein the hydrocarbon seep is a subsea seep.

37. The method of paragraph 35, wherein the sample is obtained from sediment in area with no hydrocarbon seep.

38. The method of paragraph 35, wherein the sample is obtained from sediment in an area near a paleo-seep.

39. The method of paragraph 35, wherein the sample is obtained from a water column above a hydrocarbon seep.

40. The method of paragraph 35, wherein the sample is obtained from a drill core sample.

41. The method of paragraph 35, wherein the sample is obtained from produced reservoir fluids.

42. The method of paragraph 35, wherein the sample is a first sample, and further comprising: obtaining second and third samples from two of sediment near a hydrocarbon seep, sediment in an area with no hydrocarbon seep, sediment near a paleo-seep, a water column above a hydrocarbon seep, a drill core sample, and produced reservoir fluids; using the first plurality of analyses to determine a community structure of an ecology of each of the samples; using the second plurality of analyses to determine a community function of the ecology of each of the samples; using the community structure and the community function to determine whether the ecology of each of the samples matches an anticipated characteristic of a hydrocarbon system; and when the ecology of each of the samples matches the anticipated characteristic, identifying the sample as part of the hydrocarbon system.

43. The method of paragraph 35, further comprising preserving the obtained sample at a temperature at or lower than minus 60 degrees Celsius.

44. The method of paragraph 43, wherein the temperature is at or lower than about −80 degrees Celsius.

45. The method of paragraph 35, wherein the first plurality of analyses to determine the community structure of the ecology of the sample include one or more of DNA analysis, RNA analysis, metagenomics, proteomics, transcriptomics, and lipid analysis.

46. The method of paragraph 35, wherein the second plurality of analyses to determine the community function of the ecology of the sample include three or more of DNA analysis, metagenomics, proteomics, transcriptomics, phenotypes, metabolites, organic geochemistry, inorganic geochemistry, and lipid analysis.

47. The method of paragraph 35, further comprising using the ecology of the sample to determine an aspect of the hydrocarbon system.

48. The method of paragraph 47, wherein the aspect of the hydrocarbon system is one of pressure, temperature, salinity, reservoir volume, and hydrocarbon type.

49. The method of paragraph 35, wherein the hydrocarbon system comprises a subsurface hydrocarbon reservoir with seepage to a seafloor via a fault or fracture zone.

50. The method of paragraph 35, wherein the hydrocarbon system comprises a subsurface hydrocarbon reservoir with capillary seepage to a seafloor.

51. The method of paragraph 35, wherein the hydrocarbon system comprises a region of source rock without a reservoir.

52. The method of paragraph 35, wherein the hydrocarbon system comprises one of an oil shale deposit, a shale gas deposit, and an oil sands deposit.

53. The method of any one of the paragraphs 1 to 52, wherein the hydrocarbon accumulation materiality is based on at least one of: a presence of a subsurface hydrocarbon accumulation, a type of hydrocarbons in the subsurface accumulation, a quality of hydrocarbons in the subsurface accumulation, a depth of hydrocarbons in the subsurface accumulation, a hydrocarbon/water volume ratio in the subsurface accumulation prior to escape to the surface, and a volume of the subsurface accumulation.

What is claimed is:

1. A method of determining a quality and/or volume of a subsurface hydrocarbon accumulation from a sample related thereto, the method comprising:
obtaining a sample associated with a seep from the subsurface hydrocarbon accumulation;
obtaining sample data associated with the sample, wherein the sample data comprises two or more of a noble gas signature of the sample, a hydrocarbon clumped isotope signature of the sample, and an ecology signature of the sample;
using a biogeoinformatics framework to identify one or more relationships between the obtained two or more of the noble gas signature, the hydrocarbon clumped isotope signature, and the ecology signature, wherein the identified relationships relate to the hydrocarbon accumulation materiality, and wherein identifying the one or more relationships comprises comparing the obtained two or more of the noble gas signature, the hydrocarbon clumped isotope signature, and the ecology signature with a calibration dataset that comprises two or more of noble gas signatures, hydrocarbon clumped isotope signatures, and ecology signatures for known subsurface accumulations, and wherein the biogeoinformatics framework utilizes pressure and/or temperature data to calibrate the obtained two or more of the noble gas signature, hydrocarbon clumped isotope signature, and ecology signature;
using the identified relationship to determine the quality of hydrocarbons and/or volume of hydrocarbons in the subsurface hydrocarbon accumulation; and
determining whether to access hydrocarbons from the subsurface hydrocarbon accumulation based on the determined quality of hydrocarbons and/or volume of hydrocarbons in the subsurface hydrocarbon accumulation.

2. The method of claim 1, further comprising using the identified relationship to determine a depth of hydrocarbons in the subsurface accumulation or a hydrocarbon/water volume ratio in the subsurface accumulation prior to escape to the surface.

3. The method of claim 1, further comprising:
obtaining one or more of geologic data, biological data, and geophysical data associated with the subsurface hydrocarbon accumulation; and
identifying one or more relationships between the obtained two or more of the noble gas signature, the hydrocarbon clumped isotope signature, and the ecology signature and the one or more of geologic data, biological data, and geophysical data.

4. The method of claim 1, wherein identifying one or more relationships comprises comparing the two or more of the noble gas signature, the hydrocarbon clumped isotope signature, and the ecology signature with quantitative models.

5. The method of claim 1, further comprising:
determining the hydrocarbon clumped isotope signature of the sample, wherein
determining the hydrocarbon clumped isotope signature comprises:
determining an expected concentration of isotopologues of a hydrocarbon species from the sample;
modeling, using high-level ab initio calculations, an expected temperature dependence of isotopologues present in the sample; and
measuring a hydrocarbon clumped isotope signature of the isotopologues present in the sample;
comparing the hydrocarbon clumped isotope signature with the expected concentration of isotopologues; and
using the comparison to determine one or more of whether hydrocarbons present in the sample originate directly from a source rock or whether the hydrocarbons present in the sample have escaped from a subsurface accumulation; the current equilibrium storage temperature of the hydrocarbon species in the subsurface accumulation prior to escape to the surface; and a location of the subsurface accumulation.

6. The method of claim 5, wherein determining an expected concentration of isotopologues includes determining a stochastic distribution of isotopologues of the hydrocarbon species for a given bulk isotopic signature for the species.

7. The method of claim 5, wherein the location comprises a depth.

8. The method of claim 5, wherein determining a location includes applying a thermal gradient to an equilibrium storage temperature of the subsurface accumulation.

9. The method of claim 5, further comprising determining a precise location of the subsurface hydrocarbon accumulation using a geophysical imaging technique.

10. The method of claim 9, wherein the geophysical imaging technique is seismic reflection.

11. The method of claim 1, further comprising:
characterizing the ecology signature of the sample, wherein characterizing the ecology signature comprises:
using a first plurality of analyses to determine a community structure of the sample;
using a second plurality of analyses to determine a community function of the sample; and
using the community structure and the community function to determine an ecology of the sample;
determining whether the ecology of the sample matches a characteristic ecology of a hydrocarbon system that is associated with the subsurface hydrocarbon accumulation; and
when the ecology of the sample matches the characteristic ecology, identifying the sample as party of the hydrocarbon system.

12. The method of claim 11, wherein the first plurality of analyses to determine the community structure of the sample includes one or more of DNA analysis, RNA analysis, metagenomics, proteomics, transcriptomics, and lipid analysis.

13. The method of claim 11, wherein the second plurality of analyses to determine the community function of the sample includes three or more of DNA analysis, metagenomics, proteomics, transcriptomics, phenotypes, metabolites, organic geochemistry, inorganic geochemistry, and lipid analysis.

14. The method of claim 1, further comprising:
determining the noble gas signature of the sample, wherein determining the noble gas signature comprises:
measuring or modeling an initial concentration of atmospheric noble gases present in formation water in contact with a seep associated with the subsurface hydrocarbon accumulation;

modifying the measured/modeled initial concentration by accounting for ingrowth of radiogenic noble gases during residence time of the formation water;

measuring concentrations and isotopic ratios of atmospheric noble gases and radiogenic noble gases present in the sample;

comparing the measured concentrations and isotopic ratios of the atmospheric noble gases and the radiogenic noble gases present in the sample to the modified measured/modeled concentrations of the formation water for a plurality of exchange processes;

comparing an atmospheric noble gas signature measured in the hydrocarbon phase with the modified measured/modeled concentration of the atmospheric noble gases in the formation water for the plurality of exchange processes; and using the comparison to determine at least one of a presence of a subsurface hydrocarbon accumulation, a source of the hydrocarbons in the subsurface accumulation, a type of hydrocarbons in the subsurface accumulation, a quality of hydrocarbons in the subsurface accumulation, a hydrocarbon/water volume ratio in the subsurface accumulation prior to escape to the surface, and a volume of the subsurface accumulation.

15. The method of claim 14, wherein the plurality of exchange processes include at least one of equilibrium solubility laws calibrated to reflect conditions in the subsurface accumulation, Rayleigh-style fractionation to represent the de-gassing of an oil phase, and gas stripping to represent enrichment in a gas phase.

16. The method of claim 15, wherein the conditions include at least one of reservoir temperature, pressure, formation water salinity, and oil density.

17. The method of claim 14, wherein the noble gases include at least one of helium (He), neon (Ne), argon (Ar), krypton (Kr), and xenon (Xe).

18. The method of claim 14, wherein determining a source of hydrocarbons present in the sample comprises determining whether hydrocarbons present in the sample originate directly from a source rock, or have escaped from a subsurface accumulation.

19. The method of claim 1, wherein the sample comprises one of water, oil, natural gas, sediments, rock, fluids present in sediments, fluids from rock pores, and fluids trapped in fluid inclusions.

20. The method of claim 14, further comprising characterizing non-hydrocarbon gas risk associated with the subsurface hydrocarbon accumulation.

21. The method of claim 1, wherein the hydrocarbon accumulation materiality is based on at least one of: a presence of a subsurface hydrocarbon accumulation, a type of hydrocarbons in the subsurface accumulation, a quality of hydrocarbons in the subsurface accumulation, a depth of hydrocarbons in the subsurface accumulation, a hydrocarbon/water volume ratio in the subsurface accumulation prior to escape to the surface, and a volume of the subsurface accumulation.

22. The method of claim 1, further comprising producing hydrocarbons from the subsurface hydrocarbon accumulation.

* * * * *